(12) United States Patent
Rezvani et al.

(10) Patent No.: US 10,821,134 B2
(45) Date of Patent: Nov. 3, 2020

(54) BK VIRUS SPECIFIC T CELLS

(71) Applicant: Board of Regents, The University of Texas System, Austin, TX (US)

(72) Inventors: Katy Rezvani, Houston, TX (US); Elizabeth Shpall, Houston, TX (US); Muharrem Muftuoglu, Houston, TX (US)

(73) Assignee: Board of Regents, The University of Texas System, Houston, TX (US)

( * ) Notice: Subject to any disclaimer, the term of this patent is extended or adjusted under 35 U.S.C. 154(b) by 50 days.

(21) Appl. No.: 15/982,942

(22) Filed: May 17, 2018

(65) Prior Publication Data

US 2018/0333435 A1    Nov. 22, 2018

Related U.S. Application Data

(60) Provisional application No. 62/507,735, filed on May 17, 2017.

(51) Int. Cl.
| | | |
|---|---|---|
| *A61K 35/17* | (2015.01) | |
| *A61K 39/12* | (2006.01) | |
| *C12N 5/00* | (2006.01) | |
| *A61P 31/20* | (2006.01) | |
| *C12N 5/0783* | (2010.01) | |
| *C12N 5/0784* | (2010.01) | |

(52) U.S. Cl.
CPC .............. *A61K 35/17* (2013.01); *A61K 39/12* (2013.01); *A61P 31/20* (2018.01); *C12N 5/0018* (2013.01); *C12N 5/0638* (2013.01); *C12N 5/0639* (2013.01); *C12N 2501/2307* (2013.01); *C12N 2501/2315* (2013.01); *C12N 2501/998* (2013.01); *C12N 2710/22034* (2013.01)

(58) Field of Classification Search
None
See application file for complete search history.

(56) References Cited

U.S. PATENT DOCUMENTS

| | | | |
|---|---|---|---|
| 5,641,628 A | 6/1997 | Bianchi | |
| 6,274,378 B1 | 8/2001 | Steinman et al. | |
| 6,455,299 B1 | 9/2002 | Steinman et al. | |
| 6,821,778 B1 | 11/2004 | Takamizawa et al. | |
| 7,785,875 B2 | 8/2010 | Hwang et al. | |
| 8,481,051 B2 | 7/2013 | Kuzushima et al. | |
| 9,255,243 B2 | 2/2016 | Wilson et al. | |
| 9,963,677 B2 | 5/2018 | Leen et al. | |
| 2004/0022761 A1 | 2/2004 | Banchereau et al. | |
| 2005/0028505 A1 | 2/2005 | Schumacher | |
| 2005/0106717 A1 | 5/2005 | Wilson et al. | |
| 2006/0045883 A1 | 3/2006 | Molldrem et al. | |
| 2006/0073126 A1 | 4/2006 | Shiku et al. | |
| 2008/0260701 A1 | 10/2008 | Hope | |
| 2009/0305324 A1 | 12/2009 | Kuzushima et al. | |
| 2011/0182870 A1 | 7/2011 | Leen et al. | |
| 2015/0010519 A1 | 1/2015 | Leen et al. | |
| 2015/0044258 A1 | 2/2015 | Knaus | |
| 2016/0208216 A1 | 7/2016 | Vera et al. | |
| 2016/0362658 A1 | 12/2016 | Leen et al. | |

FOREIGN PATENT DOCUMENTS

| | | |
|---|---|---|
| WO | 2005028505 A2 | 3/2005 |
| WO | 2005035728 A2 | 4/2005 |
| WO | 2007121276 A2 | 10/2007 |
| WO | 2008073313 A2 | 6/2008 |
| WO | 2009053109 A1 | 4/2009 |
| WO | 2011/028531 A1 | 3/2011 |
| WO | 2013088147 A1 | 6/2013 |
| WO | WO 2016/073595 | 5/2016 |
| WO | WO 2016/073595 A1 * | 5/2016 |

OTHER PUBLICATIONS

Geyeregger et al. Short-Term In-Vitro Expansion Improves Monitoring and Allows Affordable Generation of Virus-Specific T-Cells against Several Viruses for a Broad Clinical Application. PLoS ONE, 2013, 8(4): e59592.*
Blyth et al., "Bk Virus Specific T Cells Expanded Ex Vivo for Use in Cellular Therapy Show Multiple Antigen Specificity and Polyfunctional TH1 Responses", abstract #164, S215.
Blyth et al., "BK Virus-Specific T Cells for Use in Cellular Therapy Show Specificity to Multiple Antigens and Polyfunctional Cytokine Responses", *Transplantation*, 92(10):1077-1084, 2011.
Dasari et al., "Prophylactic and therapeutic adenoviral vector-based multivirus-specific T-cell immunotherapy for transplant patients", *Mol. Ther.*, 3:16058, 2016.
Gaundar et al., "The Generation of Clinical Grade Aspergillus Fumigatus (AF) Specific Immune Cells for Adoptive Immunotherapy", abstract #168, S216.
Gerdemann et al., "Rapidly Generated Multivirus-specific Cytotoxic T Lymphocytes for the Prophylaxis and Treatment of Viral Infections", *Am. Soc. Gene Cell Ther.*, 20(8):1622-1632, 2012.
Muftuoglu et al., "Use of Expanded Allogeneic Third Party BK Virus Specific Cytotoxic T Cells to Target Progressive Multifocal Leukoencephalopathy", *Am. Soc. Hematol.*, abstract #98495, 128(22):3365, 2016.
Olson et al., "Efficacy of Third Party BK Virus (BKV) Specific Cytotoxic T-Lymphocytes Generated by Ex Vivo Expansion for the Treatment of BKV Infection in Stem Cell Transplant Recipients, a Phase 2 Trial", *Am. Soc. Hematol.*, abstract, 128(22):504, 2016.
Bensussan et al. "Detection of membrane-bound HLA-G translated products with a specific monoclonal antibody", Proc. Natl. Acad. Sci. USA, 92:10292-10296, 1995.
Binggeli et al., American Journal of Transplantation, 2007, vol. 7, pp. 1131-1139.

(Continued)

*Primary Examiner* — Nianxiang Zou

(57) ABSTRACT

Provided herein are methods of rapidly expanding BKV-specific T cells using a peptide mixture and cytokines. Further provided herein are methods of treating polyomavirus-associated diseases by administering the BKV-specific T cells.

21 Claims, 9 Drawing Sheets

(56) References Cited

OTHER PUBLICATIONS

Blyth et al., in Blood, (Nov. 20, 2009) vol. 114, No. 22, pp. 962, Meeting Info.: 51st Annual Meeting of the American-Society-of-Hematology, New Orleans, LA, USA. Dec. 5-8, 2009, Amer Soc Hematol.
Can and Karahuseyinoglu, "Concise review: human umbilical cord stroma with regard to the source of fetus-derived stem cells", Stem Cells, 25:2886-2895, 2007.
Chakera et al., Clin Exp. Immunol2011, Sep. 156 (3): 401-409.
Dunne et al., "Selective Expansion and Partial Activation of Human NK Cells and NK Receptor-Positive T Cells by IL-2 and IL-15", Journal of Immunology, 2001, pp. 3129-3138.
Vera, Juan F., et al; "Accelerated Production of Antigen-Specific T-cells for Pre-Clinical and Clinical Applications using Gas-Permeable Rapid Expansion Cultureware (G-Rex)"; Journal of Immunotherapy, Apr. 2010, vol. 33, No. 3, pp. 305-315.
Gerdemann et al., "Cytotoxic T lymphocytes simultaneously targeting multiple tumor-associates antigens to treat EBV negative lymphoma", Molecular Therapy, Nature Publishing Group, GB, vol. 19, No. 12, Dec. 1, 2011, pp. 2258-2268.
Gerdemann et al., "Generation of Multivirus-specific T Celll's to Prevent/treat Viral Infections aftr Allogeneic Hematopoietic Stem Cell Transplant", Journal of Visualized Experiments, May 2011, vol. 51, e2736, pp. 1-6.
Gerdemann et al., "Multivirus-specific CTL for Adoptive Transfer Using In Vitro Pepmix Stimulation", Biology Blood Marrow Transplant, online Jan. 28, 2011, p. S216.
Gerdemann et al., "Nucleofection of DCs to Generate Multivirus-specific T Cells for Prevention or Treatment of Viral Infections in the Immunocompromised Host", Molecular Therapy, vol. 17, No. 9, Sep. 1, 2009, pp. 1616-1625.
Gerdemann et al., "Rapidly Generated Multivirus-specific Cytotoxic T Lymphocytes for the Prophylaxis and Treatment of Viral Infections", Molecular Therapy 2012, vol. 20, No. 8, pp. 1622-1632.
Gerdemann et al., "Safety and clinical efficacy of rapidly-generated trivirus-directed T cells as treatment for adenovirus, EBV, and CMV infections after allogeneic hematopoietic stem cell transplant", Molecular Therapy, vol. 2, No. 11, Jun. 20, 2013, pp. 2112-2121.
Hobeika et al., "Detailed analysis of cytomegalovirus (CMV)-specific T cells expanded for adoptive immunotherapy of CMV infection following allogeneic stem cell transplantation for malignant disease", Intl. Society for cellular Therapy, Cytotherapy, 2008, vol. 10, No. 3, pp. 289-302.
International Preliminary Report on Patentablility dated Feb. 10, 2014, during prosecution of International Application No. PCT/GB2012/053113.
International Search Report and Written Opinion issued in International Application No. PCT/US2010/46505, dated Oct. 14, 2010.
Y E Z, et al; In Vitro expansion and Charcterization of Dendritic Cells Derived from Human Bon Marroe CD34+ Cells; Bone Marrow Transpaln, 1996, v 18. 997-1008.
Jennes et al., "Enhanced ELISPOT detection of antigen-specific T cell responses from cryopreserved specimens with addition of both IL-7 and IL-15 the Amplispot assay" Journal of Immunological Methods, 2002, vol. 270, pp. 99-108.
Kedl et al; "T Cells Compete for Antigen-bearing Antigen-presenting Cells"; J.P. Med.—The Rockfeller University Press—vol. 192, No. 8, Oct. 16, 2002.
Kedl et al; "T Cells Down-Modulate Peptide-MHC Complexes on APCs in vivo"; Published online: Dec. 3, 2001, DOI: 10.1 038/ni/742; 2002 Nature Publishing Group.
Khanna et al., Blood, Jul. 2011, vol. 118, No. 4, pp. 1121-1131.
Lapteva and Vera "Optimization Manufacture of Virus- and Tumor-Specific T Cells", Stem Cells International, Apr. 26, 2011, vol. 2011, pp. 1-8.
Leen et al., "Cytotoxic lymphocyte (CTL) therapy for the treatment of EBV negative tumors", Abstract, International Society for Cell and Gene Therapy of Cancer Annual Meeting held in Cork, Ireland, presented Sep. 4, 2009.
Leen et al., "Identification of hexon-specific CD4 and CDS T-cell epitopes for vaccine and immunotherapy," Journal of Virology, 82(1):546-554, 2008.
Vella et al., "Cytokine-induced survival of activated T cells in vitro and in vivo", Proc. Natl. Acad. Sci. USA 95, Immunology, Mar. 1998, vol. 95, pp. 3810-3815.
Leen et al., "Overcoming antigenic competition to produce multispecific cytotoxic T lymphocyte lines for adoptive transfer," Poster, 6th Annual Dan L. Duncan Cancer Center Symposium, Baylor College of Medicine, Feb. 2009, No. 374, p. 134.
Leen et al., Nature Medicine, 2006, vol. 12, No. 10, pp. 1160-1166.
Liao et al., "Transfection of RNA encoding tumor antigens following maturation of dendritic cells leads to prolonged presentation of antigen and the generation of high-affinity tumor-reactive cytotoxic T lymphocytes", Molecular Therapy, May 1, 2004, vol. 9, No. 5, pp. 757-764.
Lim et al. Journal of Translational Medicine 2009, vol. 7:72, pp. 1-11.
Maecker et al., Journal of Immunological Methods, 2001, vol. 55, pp. 27-40.
Montes et al., "Optimum in vitro expansion of human antigen-specific CD8+ T cells for adoptive transfer therapy", British Society for Immunology, Clinical and Experimental Immunology, 2005, vol. 142, pp. 292-302.
Morandi et al., "Tumor mRNA-Transfected Dendritic Cells Stimulate the Generation of CTL that Recognize Neuroblastoma-Associated Antigens, Kill Tumor Cells: Immunotherapeutic Implications", Neoplasia, Oct. 1, 2006, vol. 8, No. 10, pp. 833-842.
Na et al., "Human Bone Marrow as a Source of Multifunctional CMV-Specific CD4+ T Cells for Adoptive Cell Therapy" Blood, 2007, vol. 110, p. 2973.
Nair et al, "Induction of tumor-specific cyototoxic T lymphocytes in cancer patients by autologous tumor RNA-transfected dendritic cells", Annals of Surgery, Apr. 1, 2002, vol. 235, No. 4, pp. 540-549.
Ramaswami et al., Clin Vaccine Immunol, Published on line Mar. 2, 2011, vol. 18, No. 5 815-824.
Suneetha et al., Journal of Immunological Methods, 2009, vol. 342, No. 1-2, pp. 33-48.
Testa et al: "MHC Class I-Presented T Cell Epitopes Identified by Immunoproteomics Analysis are Targets for a Cross Reactive Influenza-Specific T Cell Response", PLOS ONE, vol . 7, No. 11, Nov. 7, 2012 (Nov. 7, 2012), p. e48484.
Trivedi et al., "Generation of CMV-specific T lymphocytes using protein-spanning pools of pp65-derived overlapping pentadecapeptides for adoptive immunotherapy", Blood, Apr. 1, 2005, vol. 105, No. 7, pp. 2793-2794.
van Montfoort et al., "Antigen storage compartments in mature dendritic cells facilitate prolonged cytotoxic T lymphocyte cross-priming capacity", PNAS, Apr. 21, 2009, vol. 106, No. 16, pp. 6730-6735.
Calarota et al. "Detection of Epstein-Barr vires-specific memory CD4+T cells using a peptide-based cultured enzyme-linked immunospot assay", Immunology, 2013: 139: 533-544.
Jeffes III et al. "Therapy of recurrent high grade gliomas with surgery, and autologous mitogen activated IL-2 stimulated killer (MAK) Lymphocytes: I. Enchancement of MAK lytic activity and cytokine production by PHA and clinical use of PHA" Journal of Neuro-Oncology, 1993, vol. 15, pp. 141-155.

* cited by examiner

BK VIRUS SPECIFIC T CELLS

The present application claims the priority benefit of U.S. Provisional Application Ser. No. 62/507,735, filed May 17, 2017, the entire contents of which are hereby incorporated by reference.

BACKGROUND

1. Field

The present invention relates generally to the fields of immunology and medicine. More particularly, it concerns methods of generating polyomavirus-specific T cells and methods of their use.

2. Description of Related Art

Stem cell transplantation can be used to treat patients having leukemia or other disorders. Transplanted donor T cells (lymphocytes) exert strong alloimmune graft-versus leukemia (GVL) and other anti-tumor effects. However, these donor cells can also cause potentially lethal graft-versus-host disease (GVHD), requiring post-transplant immunosuppression. As a result of such immunosuppression, patients are more likely to contract a potentially fatal infection, such as a cytomegalovirus (CMV) infection or BK virus infection, and are less likely to be cured of their malignant disease.

For example, clinical manifestations of BKV hemorrhagic cystitis (HC) following hematopoietic stem cell transplantation (HSCT) range from microscopic hematuria to bladder hemorrhage and renal failure. Pharmacologic treatments for HC have limited efficacy and significant adverse effects.

The transfer of T lymphocytes specific for leukemia cells or micro-organism antigens would be useful because therapeutic immune effects would be enhanced while GVHD reactions would not be induced. However, currently available methods for isolating and expanding antigen-specific T cells are costly and inefficient. A study by Gerdmann et al. disclosed the expansion of BKV cytotoxic T lymphocytes (CTLs) with a combination of IL-4 and IL-7 using two BKV peptides, VP-1 and Large T antigen (Gerdmann et al., 2012). However, the efficiency of producing BKV $CD4^+$ and $CD8^+$ T cells by this method was very low with less than 1% of the cells produced being $CD8^+IFN\gamma^+$ T cells. As a high number of robust BKV-specific T cells is needed to infuse patients for treatment, there is an unmet need for methods of efficiently expanding robust BKV specific T cells at a reproducibly high frequency.

SUMMARY

In a first embodiment, the present disclosure provides an ex vivo method for generating BKV-specific T cells comprising obtaining a starting population of T cells; and culturing the starting population of T cells in the presence of IL-7, IL-15, and a mixture of peptides, wherein the mixture of peptides comprises overlapping peptides spanning at least 3 immunodominant proteins selected from the group consisting of small T antigen, large T antigen, VP1, VP2, and VP3, thereby generating BKV-specific T cells. In some aspects, the BKV-specific T cells are further defined as cytotoxic T cells (CTLs).

In certain aspects, the starting population of T cells comprises peripheral blood mononuclear cells (PBMCs) or lymphocytes. In some aspects, culturing is for 8-14 days, such as for 10-12 days, such as 10, 11, or 12 days.

In particular aspects, the culture does not comprise a second population of cells pre-stimulated with the mixture of peptides. In some aspects, the pre-stimulated cells are further defined as antigen presenting cells, such as dendritic cells, monocytes, or B lymphocytes.

In some aspects, the starting population of T cells are cultured in the presence of overlapping peptides spanning 4 of the immunodominant proteins. In particular aspects, the starting population of T cells are cultured in the presence of overlapping peptides spanning small T antigen, large T antigen, VP1, VP2, and VP3. In some aspects, the overlapping peptides have a length of 10-20 amino acids, such as 10, 11, 12, 13, 14, 15, 16, 17, 18, 19 or 20 amino acids. In particular aspects, the overlapping peptides have a length of 15 amino acids.

In certain aspects, the culture further comprises IL-2. In some aspects, the IL-2 is present at a concentration of 10 iU/mL to 200 iU/mL, such as 20, 30, 40, 50, 75, 100, 150, or 200 iU/mL. In additional aspects, the method further comprises selecting for CD4 and/or CD8-positive T cells.

In some aspects, the method further comprises selecting for $IFN\gamma$- and/or IL-2-secreting T cells. In certain aspects, the percentage of $IFN\gamma$-secreting cells is at least 15% of the BKV-specific T cells, such as at least 16, 17, 18, 19, 20, 21, 22, 23, 24, or 25% of the BKV-specific T cells. In particular aspects, the percentage of IL-2-secreting cells is at least 5% of the BKV-specific T cells, such as at least 6, 7, 8, 9, 10, 11, 12, 13, 14, or 15% of the BKV-specific T cells. In some aspects, the percentage of $IFN\gamma$- and IL-2-secreting cells is at least 5% of the BKV-specific T cells, such as at least 6, 7, 8, 9, 10, 11, 12, 13, 14, or 15% of the BKV-specific T cells.

In certain aspects, the peptide mixture and cytokines are not changed after initiation of the culturing step of the expansion.

In some aspects, the BKV-specific T cells are human. In certain aspects, the BKV-specific T cells are engineered to have decreased or essentially no expression of glucocorticoid receptor. In some aspects, the BKV-specific T cells are engineered using one or more guide RNAs and a Cas9 enzyme. In certain aspects, the BKV-specific T cells are engineered to express a chimeric antigen receptor (CAR) and/or a T cell receptor (TCR).

Further provided herein is a pharmaceutical composition comprising BKV-specific T cells produced by the methods of the present embodiments and aspects thereof. In another embodiment there is provided a composition comprising an effective amount of BKV-specific T cells of any one of present embodiments and aspects thereof for the treatment of a polyomavirus-associated disease in a subject. Further provided if the use of a composition comprising an effective amount of BKV-specific T cells of the present embodiments and aspects thereof for the treatment of a polyomavirus-associated disease in a subject.

In another embodiment, there is provided a method for treating a polyomavirus-associated disease in a subject comprising administering an effective amount of the BKV-specific T cells of the present embodiments and aspects thereof to the subject. In some aspects, the BKV-specific T cells are allogeneic. In certain aspects, the BKV-specific T cells are autologous. In certain aspects, the subject is infected with BK virus or JC virus. In some aspects, the subject is administered the BKV-specific T cells more than once. In certain aspects, the polyomavirus-associated disease is progressive multifocal leukoencephalopathy (PML), Merkel cell carcinoma (MCC), polyomavirus-associated nephropathy (PVAN), hemorrhagic cystitis, JC encephalitis, or trichodysplasia spinulosa (TS).

In some aspects of the above embodiments, the BKV-specific T cell dose is between 100-100,000 cells/kg, such as about 200, 300, 400, 500, 600, 700, 800, 900, 1000, 2000, 3000, 5000, 10000, 15000, 20000, 25000, 30000, 40000, 50000, 60000, 70000, 80000, 90000, or 100000 cells/kg. In certain aspects, the BKV-specific cells are administered intravenously. In other aspects, the BKV-specific cells may be administered directly to the central nervous system.

In some aspects, the BKV-specific T cells are HLA-matched to the subject. In particular aspects, the BKV-specific T cells are matched to the subject on at least one HLA allele, such as at 2, 3, 4, 5, or 6 HLA alleles. In particular aspects, HLA-matching is further defined as HLA-matching at class I or class II genes. In some aspects, the MHC class I and II genes are HLA-A, HLA-B and/or DRB1.

In additional aspects, the method further comprises immunodepleting the subject prior to administering the BKV-specific T cells. In some aspects, the method further comprises administering at least a second therapeutic agent. In some aspects, the at least a second therapeutic agent comprises chemotherapy, immunotherapy, surgery, radiotherapy, or biotherapy. In certain aspects, the BKV-specific T cells and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion. In some aspects, the second therapeutic agent is an anti-viral or immunomodulatory agent, such as a cytokine or interferon.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 3A) Pre-expansion frequency of BKV-specific CD4 and CD8 T cells producing IL-2 is 0.038% and producing IFNγ is 0.005%. (FIG. 3B) Post-expansion frequency of BKV-specific T cells expanded with the 5 peptide mix and various cytokines as indicated. (FIG. 3C) Post-expansion frequency of BKV-specific T cells expanded with the 5 peptide mix and IL-2+IL-7+IL-15.

(FIG. 5A) Response in patients is associated with BKV CTL expansion. (FIG. 5B) PCR analysis of urine samples from responders.

DESCRIPTION OF ILLUSTRATIVE EMBODIMENTS

Figure 1:
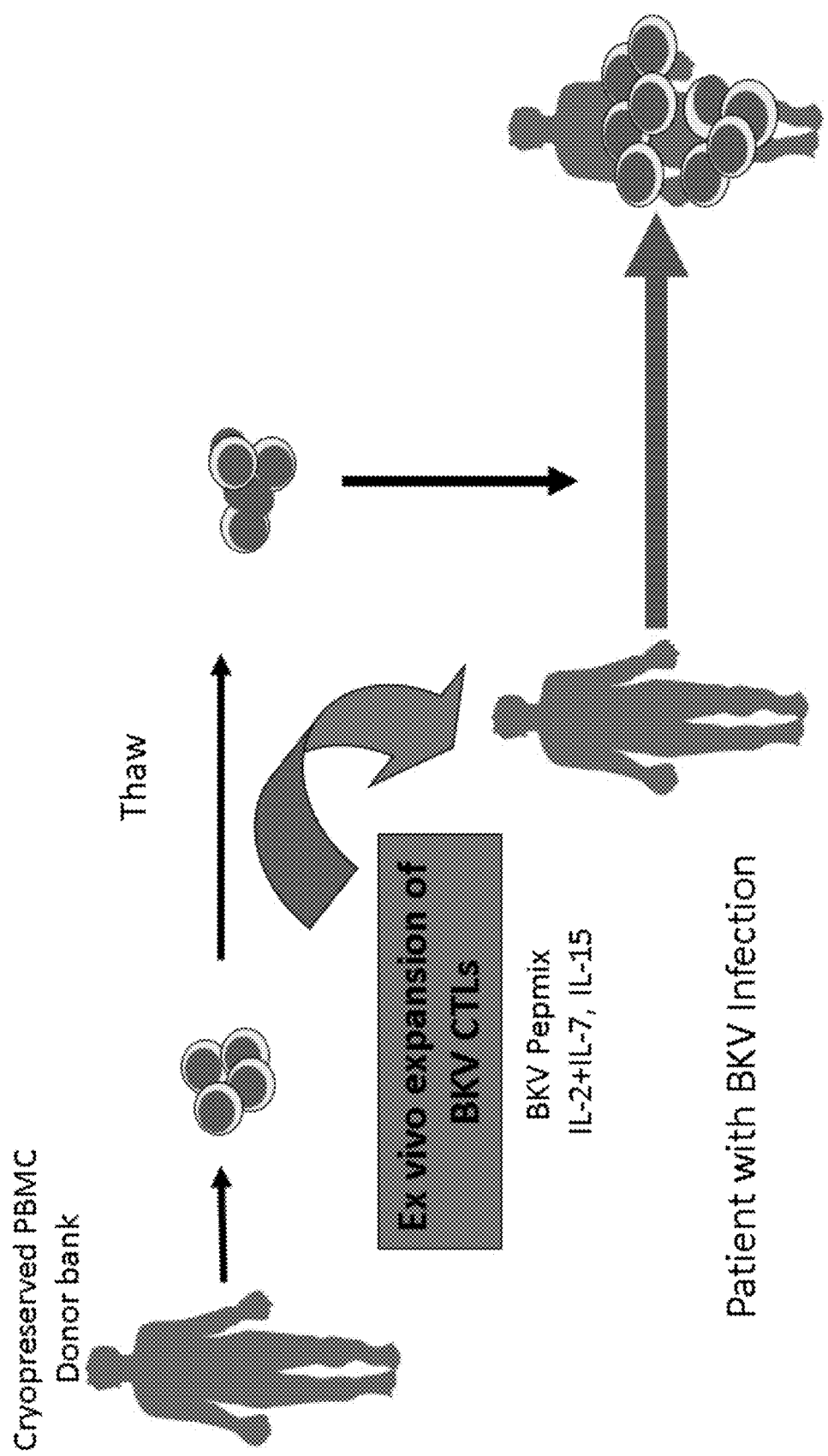
FIG. 1: Schematic depicting BKV-specific CTL lines generated by ex vivo expansion in stem cell transplant recipients with active BK infection.

In certain embodiments, the present disclosure provides a highly efficient method for the generation of potent BKV-specific T cells. The BKV-specific T cells may be generated by directly stimulating a starting population of T cells, such as mononuclear cells enriched from healthy donor or patient-derived blood or buffy coat, with a BKV peptide mix comprising overlapping peptides from capsid proteins VP1, VP2, VP3, large T antigen (LT) and small T antigen (ST) (e.g., PepMix™, JPT) in the presence of IL-2, IL-7 and IL-15 for less than 15 days, such as about 10-14 days, particularly for 10 days. This method allowed generation of IFNγ- and IL-2-secreting BKV-specific T cells independent of the HLA type of the donor. However, it was also determined that the BKV-specific T cells produced by the present methods are biased toward a CD4$^+$ population. Thus, the patient may be HLA-matched to the cells based on MHC Class II genes.

At the end of culture, the cells are harvested and cryopreserved until use. Importantly, the frequency of BKV-CTLs in this product is significantly higher than any currently available methods. In addition, the present method produces a greater number of BKV-specific T cells in a short period of time which are highly functional and continue to persist when administered in vivo. Importantly, the present method directly produces BKV-specific T cells without the use of antigen-presenting cells such as monocytes (e.g., PBMCs), B lymphocytes, or dendritic cells stimulated (i.e., previously incubated) with the BKV antigen.

The BKV-specific T cells may be engineered to redirect their specificity by expressing a chimeric antigen receptor (CAR) and/or a T cell receptor (TCR). In addition, the BKV-specific T cells may be genetically modified to make them glucocorticoid resistant, such as by using the CRISPR-Cas system to knockdown expression of glucocorticoid receptor.

Further provided herein are methods for the use of the BKV-specific T cells for the treatment of a variety of polyomavirus-associated diseases and infections including BKV hemorrhagic cystitis which is a common complication in the immune compromised host, such as after hematopoietic stem cell or solid organ transplant or after chemotherapy. In addition, JC virus-mediated progressive multifocal encephalopathy, such as for patients with cancer or following transplantation or treated with biologic agents including natalizumab multiple sclerosis. The BKV-specific T cells may also be used for the treatment of Merkel cell carcinoma and other BKV-related cancers including but not limited to prostate cancer. Further applications of the BKV-specific T cells include the treatment or prevention of graft rejection after renal transplantation. The BKV-specific T cells may be administered in combination with a second therapy, such as an anti-cancer therapy. For example, the BKV-specific T cells may be administered as an adjuvant to chemotherapy or radiotherapy for the treatment of Merkel cell carcinoma or other polyomavirus-associated cancers.

In the present studies, 19 patients were treated with HLA-matched BKV-specific CTL lines (BKV-CTLs) generated by ex vivo expansion as detailed herein. Dramatic reduction in symptomatic toxicities including dysuria, and painful hematuria/clots occurred in the first week after infusion in the majority of patients. There were no infusion-related adverse effects. Based on end-organ response, the response rate was 77%. In addition, two patients with PML for which there is no effective therapy, were treated with the super-potent BKV-CTLs. One patient who was ataxic with progressive weakness and neurologic deterioration achieved a complete response and is back at work with a normal neurologic exam; the other achieved a partial response. Thus, the present disclosure provides a virus-specific product that is a highly competitive and efficacious therapy.

I. DEFINITIONS

The term "cell" is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells or genetically modified cells).

The term "T cell" refers to T lymphocytes, and includes, but is not limited to, $\gamma:\delta^+$ T cells, NK T cells, CD4$^+$ T cells and CD8$^+$ T cells. CD4$^+$ T cells include $T_H0$, $T_H1$ and $T_H2$ cells, as well as regulatory T cells ($T_{reg}$). There are at least three types of regulatory T cells: CD4+CD25+$T_{reg}$, CD25 $T_H3$ $T_{reg}$, and CD25 $T_R1$ $T_{reg}$. "Cytotoxic T cell" refers to a T cell that can kill another cell. The majority of cytotoxic T cells are CD8+ MHC class I-restricted T cells, however some cytotoxic T cells are CD4+. In preferred embodiments, the T cell of the present disclosure is CD4+ or CD8+.

A "leukocyte" refers to cells in the blood, also termed "white cells," that are involved in defending a subject against infective organisms and foreign substances. Leukocytes are produced in the bone marrow. There are five main types, subdivided between two main groups: polymorphomnuclear leukocytes (neutrophils, eosinophils, basophils) and mononuclear leukocytes (monocytes and lymphocytes). Generally, when a subject has an infection, the production of leukocytes increases. A "lymphocyte: is a type of white blood cell involved in the immune defenses of the body. There are two main types of lymphocytes: B-cells and T-cells.

A "monocyte" is a large white blood cell in the blood that ingests microbes or other cells and foreign particles and proteins. When a monocyte passes out of the bloodstream and enters tissues, it develops into a macrophage.

As used herein, the term "antigen" is a molecule capable of being bound by an antibody or T-cell receptor. An antigen may generally be used to induce a humoral immune response and/or a cellular immune response leading to the production of B and/or T lymphocytes.

An "epitope" is the site on an antigen recognized by an antibody as determined by the specificity of the amino acid sequence. Two antibodies are said to bind to the same epitope if each competitively inhibits (blocks) binding of the other to the antigen as measured in a competitive binding assay. Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

An "autoimmune disease" refers to a disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

The term "polyomavirus" refers to a genus of nonenveloped viruses having an icosahedral capsid. The genome of polyomaviruses includes non-structural proteins (large T antigen and small t antigen), a non-coding region including an origin of replication and promoters, and structural proteins (VP1, VP2, and VP3). Polyomaviruses include but are not limited to BK polyomavirus, JC polyomavirus, Merkel cell polyomavirus, and simian virus 40 (SV40). Related human polyomaviruses WU virus (Gaynor et al, 2007), KI virus (Allander et al, 2007), and trichodysplasia spinulosa-associated polyomavirus (van der Meij den et al, 2010) have been reported in clinical samples.

A "BK virus (BKV)-specific T cell" refers to a CD8 or CD4 lymphocyte that binds a BK virus antigen.

The term "specifically binds" means to selectively bind with a single binding affinity for a particular antigen/epitope with which it immunoreacts. Examples include antigens and T cells that selectively immunoreact with a target antigen. In a particular example of specific binding, a T cell receptor on a target antigen-specific T cell specifically recognizes and reacts with a target antigen presented on an APC, such as an MEW complex, wherein the binding is a non-random binding reaction between the T cell receptor and a target antigenic determinant. In a specific example, the desired binding specificity of a target antigen-specific T cell is determined from the reference point of the ability of the T cell receptor on the target antigen-specific T cell to bind to an APC presenting the target antigen, but not an unrelated antigen, and therefore distinguish between two different antigens.

The term "antigen presenting cell (APC)" refers to a cell that carries on its surface MEW class I or class II molecules capable of presenting an antigen in the context of the MHC molecule to T cells. APCs include, but are not limited to, monocytes, macrophages, dendritic cells, B cells, and Langerhans cells.

The term "graft-versus-host disease (GVHD)" refers to an incompatibility reaction in a subject (host) of low immunological competence who has been the recipient of immunologically competent lymphoid tissue from a donor who is immunologically different from the recipient. The reaction is the result of the action of the transplanted cells against those host tissues that possess an antigen not found in the donor. Acute and chronic GVHD are a major cause of morbidity and mortality among hematopoietic stem cell transplant recipients. Symptoms can include skin rash, intestinal problems similar to colitis, and liver dysfunction The term "haplotyping or tissue typing" refers to a method used to identify the haplotype or tissue types of a subject, for example by determining which HLA locus (or loci) is expressed on the lymphocytes of a particular subject. The HLA genes are located in the major histocompatibility complex (MHC), a region on the short arm of chromosome 6, and are involved in cell-cell interaction, immune response, organ transplantation, development of cancer, and susceptibility to disease. There are six genetic loci important in transplantation, designated HLA-A, HLA-B, HLA-C, and HLA-DR, HLA-DP and HLA-DQ. At each locus, there can be any of several different alleles.

A widely used method for haplotyping uses the polymerase chain reaction (PCR) to compare the DNA of the subject, with known segments of the genes encoding MHC antigens. The variability of these regions of the genes determines the tissue type or haplotype of the subject. Serologic methods are also used to detect serologically defined antigens on the surfaces of cells. HLA-A, —B, and -C determinants can be measured by known serologic techniques. Briefly, lymphocytes from the subject (isolated from fresh peripheral blood) are incubated with antisera that recognize all known HLA antigens. The cells are spread in a tray with microscopic wells containing various kinds of antisera. The cells are incubated for 30 minutes, followed by an additional 60-minute complement incubation. If the lymphocytes have on their surfaces antigens recognized by the antibodies in the antiserum, the lymphocytes are lysed. A dye can be added to show changes in the permeability of the cell membrane and cell death. The pattern of cells destroyed by lysis indicates the degree of histologic incompatibility. If, for example, the lymphocytes from a person being tested for HLA-A3 are destroyed in a well containing antisera for HLA-A3, the test is positive for this antigen group.

An "immune response" refers to a change in immunity, for example, a response of a cell of the immune system, such as a B cell, T cell, or monocyte, to a stimulus. In one example, the response is specific for a particular antigen (an "antigen-specific response"), such as a target antigen which has been selected for therapeutic purposes as a target of the immune response. In one example, an immune response is a T cell response, such as a $CD4^+$ response or a $CD8^+$ response. In another example, the response is a B cell response, and results in the production of specific antibodies. In a particular example, an increased or enhanced immune response is an increase in the ability of a subject to fight off a disease, such as a viral infection or tumor. Immune synapse: The region of association between an APC and an antigen-specific T cell. In a specific example, it is the complex formed between an antigen/WIC complex on an APC and the T cell receptor on the antigen-specific T cell.

A "parameter of an immune response" is any particular measurable aspect of an immune response, including, but not limited to, cytokine secretion (IL-6, IL-10, and/or IFN-γ), chemokine secretion, altered migration or cell accumulation, immunoglobulin production, dendritic cell maturation, regulatory activity, number of immune cells and proliferation of any cell of the immune system. Another parameter of an immune response is structural damage or functional deterioration of any organ resulting from immunological attack. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. Similarly, an inhibition or decrease in a parameter of the immune response is a significant decrease in this parameter as compared to a control. Specific, non-limiting examples of a substantial decrease are at least about a 50% decrease, at least about a 75% decrease, at least about a 90% decrease, at least about a 100% decrease, at least about a 200% decrease, at least about a 300% decrease, and at least about a 500% decrease. A statistical test, such as a non-parametric ANOVA, or a T-test, can be used to compare differences in the magnitude of the response induced by one agent as compared to the percent of samples that respond using a second agent. In some examples, p≤0.05 is significant, and indicates that the chance that an increase or decrease in any observed parameter is due to random variation is less than 5%. One of skill in the art can readily identify other statistical assays of use.

The term "immunodeplete" refers to a decrease the number of lymphocytes, such as $CD4^+$ or $CD8^+$ cells, in a subject. In particular examples, immunodepletion decreases the number of lymphocytes in a subject by at least 50%, such as at least 75%, at least 80%, at least 90%, at least 95%, at least 99%, or even 100%. Specific immunodepletion refers to immunodepletion of a particular lymphocyte, such as a T cell involved in the mediation of disease (such as GVHD). Immuno-depleting agent: One or more compounds, when administered to a subject, result in a decrease in the number of cells of the immune system (such as lymphocytes) in the subject. Examples include, but are not limited to, chemotherapeutic agents, monoclonal antibodies, radiation, and other therapies disclosed herein.

"Interferon-gamma (IFN-γ)" refers to a protein produced by T lymphocytes in response to specific antigen or mitogenic stimulation. The term includes naturally occurring IFN-γ peptides and nucleic acid molecules and IFN-γ fragments and variants that retain full or partial IFN-γ biological activity. Sequences for IFN-γ are publicly available (for example, exemplary IFN-γ mRNA sequences are available from GenBank Accession Nos: BC070256; AF506749; and J00219, and exemplary IFN-γ protein sequences are available from GenBank Accession Nos: CAA00226; AAA72254; and 0809316A).

"Interleukin (IL)-2" refers to a growth factor for all subpopulations of T-lymphocytes. It is an antigen-unspecific proliferation factor for T-cells that induces cell cycle progression in resting cells, and allows clonal expansion of activated T-lymphocytes. The term includes naturally occurring IL-2 peptides and nucleic acid molecules and IL-2 fragments and variants that retain full or partial IL-2 biological activity. Sequences for IL-2 are publicly available (for example, exemplary IL-2 mRNA sequences are available from GenBank Accession Nos: BC066254; BC066257; E00978; and NM_ 053836, and exemplary DL-2 protein sequences are available from GenBank Accession Nos: AAD14263; AAG53575; and AAK52904).

The term "culturing" refers to the in vitro maintenance, differentiation, and/or propagation of cells in suitable media. By "enriched" is meant a composition comprising cells present in a greater percentage of total cells than is found in the tissues where they are present in an organism.

An "isolated" biological component (such as a portion of hematological material, such as blood components) refers to a component that has been substantially separated or purified away from other biological components of the organism in which the component naturally occurs. An isolated cell is one which has been substantially separated or purified away from other biological components of the organism in which the cell naturally occurs. For example, an isolated antigen-specific T cell population is a population of T cells that recognize a target antigen and which are substantially separated or purified away from other blood cells, such as other T cells.

The term "therapeutically effective amount" refers to an amount sufficient to produce a desired therapeutic result, for example an amount of purified target antigen-specific T cells sufficient to increase an immune response against the target antigen in a subject to whom the cells are administered. In particular examples, it is an amount effective to increase an immune response in a subject by at least 10%, for example at least 20%, at least 30%, at least 40%, at least 50%, or even at least 75%.

The term "transplantation" refers to the transfer of a tissue, cells, or an organ, or a portion thereof, from one subject to another subject, from one subject to another part of the same subject, or from one subject to the same part of the same subject. In one example, transplantation of antigen-specific T cells, such as a purified population of antigen-specific T cells, into a subject involves removal of blood from the subject, selection and expansion of the target antigen-specific T cells ex vivo, and introduction of the purified target antigen-specific T cells into the same or a different subject.

An allogeneic transplant is transplantation from one individual to another, wherein the individuals have genes at one or more loci that are not identical in sequence in the two individuals. An allogeneic transplant can occur between two individuals of the same species, who differ genetically, or between individuals of two different species. An autologous transplant is transplantation of a tissue, cells, or a portion thereof from one location to another in the same individual, or the removal of a tissue such as bone marrow derived stem cells, storage of the cells at low temperature, and reinfusion into the same individual at a later time. A syngeneic or congenic transplant is the transfer of a tissue or a portion thereof from one individual to another, wherein the two individuals are genetically identical.

The term "subject" or "patient" refer to either a human or non-human, such as primates, mammals, and vertebrates. In particular embodiments, the subject is a human.

The term "treatment" refers to a therapeutic intervention that ameliorates a sign or symptom of a disease or pathological condition, such a sign or symptom related to immune suppression, such as decreasing symptoms associated with an infection, halting the progression of a tumor, reducing the size of a tumor, or even elimination of a tumor. Treatment can also induce remission or cure of a condition, such as an infection, GVHD, or a tumor. In particular examples, treatment includes preventing a disease, for example by inhibiting the full development of a disease, such as preventing development of an infection or GVHD in a subject who received a transplant. Prevention of a disease does not require a total absence of disease. For example, a decrease of at least 50% can be sufficient. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

A "peptide library," "mixture of peptides" or "peptide mixture" are used interchangeably herein to refer to a plurality of peptides derived from BKV immunodominant proteins including large T antigen, small T antigen, VP1, VP2, and/or VP3. The peptides may be overlapping at one or more amino acids of the immunodominant protein sequence.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

II. BK VIRUS-SPECIFIC T CELLS

Certain embodiments of the present disclosure concern BKV-specific T cells, particularly cytotoxic T cells (CTLs). In some embodiments, there are provided methods of rapidly expanding BKV-specific T cells from a starting population of T cells using a peptide mixture and a unique cytokine combination which directly produces potent BKV-specific T cells that may be used for the treatment of a wide variety of polyomavirus-associated diseases including infections in immunocompromised subjects.

A. Starting Population of T Cells

The starting population of T cells may be isolated from subjects, particularly human subjects. The starting population of T cells can be isolated and expanded from a donor sample, such as an allogeneic sample, or from the subject who will receive the cells (i.e., autologous). The starting population of T cells can be obtained from a subject of interest, such as a subject suspected of having a particular disease or condition, a subject suspected of having a predisposition to a particular disease or condition, or a subject who is undergoing therapy for a particular disease or condition. The starting population of T cells can be collected from any location in which they reside in the subject including, but not limited to, blood, cord blood, spleen, thymus, lymph nodes, and bone marrow. The isolated starting population of T cells may be used directly, or they can be stored for a period of time, such as by freezing.

The starting population of T cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors. In particular embodiments, the starting population of T cells are isolated from blood, such as peripheral blood or cord blood. In some aspects, starting population of T cells isolated from cord blood have enhanced immunomodulation capacity, such as measured by CD4- or CD8-positive T cell suppression. In specific aspects, the starting population of T cells are isolated from pooled blood, particularly pooled cord blood, for enhanced immunomodulation capacity. The pooled blood may be from 2 or more sources, such as 3, 4, 5, 6, 7, 8, 9, 10 or more sources (e.g., donor subjects).

When the population of immune cells is obtained from a donor distinct from the subject, the donor is preferably allogeneic, provided the cells obtained are subject-compatible in that they can be introduced into the subject. Allogeneic donor cells may or may not be human-leukocyte-antigen (HLA)-compatible.

In some aspects, the cells are human cells. The cells typically are primary cells, such as those isolated directly from a subject and/or isolated from a subject and frozen cells. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., $CD4^+$ and/or $CD8^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

Generally, the starting cell populations are isolated from blood drawn from a subject, for example using apheresis (e.g., leukapheresis) or venous puncture. In one example, blood is obtained from a donor subject, such as an HLA-matched donor or the same subject who is to receive the antigen-specific T cells (recipient subject). In one example, an HLA-matched donor is one that matches at least 1/6, such as 2/6, 3/6, 4/6 or particularly 5/6 or 6/6, of the HLA loci (such as the A, B, and DR loci). In particular examples, the HLA-matched donor is a first degree relative. Monocytes can be isolated from blood obtained from the subject using methods known in the art. In one example, monocytes are obtained by elutriation of monocytes. In another example, monocytes are obtained from peripheral blood mononuclear cells (PBMCs) using a kit to deplete nonmonocytic cells (for example from Miltenyi Biotec, Auburn, Calif.) or by positive selection using anti-CD14 magnetic beads as recommended by the manufacturer (Miltenyi Biotec). In another example, PBMCs are prepared by centrifugation over a Ficoll-Paque (Pharmacia, Uppsala, Sweden) density gradient and the monocytes separated from lymphocytes by counterflow centrifugation (for example using the J6-MC elutriator system; Beckman Instruments, Palo Alto, Calif.) or centrifugation on a continuous Percoll (Pharmacia, Piscataway, N.J.) density gradient.

Similarly, lymphocytes can be isolated from blood obtained from the subject using methods known in the art. In one example, lymphocytes are collected by elutriation of the lymphocytes. B cells can also be depleted. In another example, PBMCs are prepared by centrifugation over a Ficoll-Paque density gradient and the lymphocytes separated from monocytes as described above.

In some examples, a monocyte/lymphocyte population (a leukocyte pack or peripheral blood leukocytes (PBL)) is isolated from a subject. PBLs can be obtained by incubation of citrated blood in a medium that lyses erythrocytes, and removal of the lysed cells, thereby generating a PBL population. In one example, blood is incubated in $NH_4Cl$ buffer (0.15 M $NH_4Cl$, 10 mM $NaHCO_3$ [pH 7.4]) for 5 minutes at 4° C. (this can be repeated three times), followed by a wash in $Ca^{2+}$—$Mg^{2+}$-free phosphate-buffered saline (PBS-A) supplemented with 0.035% (wt/vol) EDTA and centrifugation to remove the lysed erythrocytes. However, this method is exemplary, and other methods known to those of skill in the art can also be utilized. The resultant monocyte, lymphocyte, or monocyte/lymphocyte product can be cryopreserved prior to use, using standard methods (for example using a combination of Pentastarch and DMSO). In some examples, cells are cryopreserved in aliquots of 5 to $200 \times 10^6$ cells/vial, such as $6\text{-}10 \times 10^6$ monocytes/vial, such as $50\text{-}200 \times 10^6$ lymphocytes/vial, such as $10\text{-}50 \times 10^6$ PBL/vial. To qualify for cryopreservation, the cell culture ideally contains predominately monocyte, lymphocyte, or monocyte/lymphocyte cells by flow cytometry. Sterility of the population need not be determined at this stage of the target antigen-specific T cells generation procedure; such a determination can occur after the final co-culture of cells. Methods for obtaining other APC populations, such as dendritic and B lymphoblastoid cells, are known in the art. For example, the Blood Dendritic Cell Isolation Kit II (Miltenyi Biotec Inc., Auburn, Calif.) can be used to obtain dendritic cells from blood according to the manufacturer's instructions or by culture from blood cells using the method of Wong et al. (*Cytotherapy,* 4: 65-76, 2002, herein incorporated by reference). B lymphoblastoid cells can be cultured from peripheral blood, for example using the method of Tosato (Current Protocols in Immunology, Ed Coligan et al, Wiley, 1994, 7.22.1, herein incorporated by reference).

B. Expansion of BKV-Specific T Cells

The methods of the present disclosure may comprise exposing the starting population of T cells, such as the buffy coat of isolated peripheral blood mononuclear cells (PBMCs), to a peptide library (i.e., mixture) and cytokines for a period of time sufficient to expand BKV-specific T cells. The peptide library may comprise overlapping peptides spanning 3, 4, or 5 of the immunodominant proteins small T antigen, large T antigen, VP1, VP2, and VP3. In particular aspects, the peptide library comprises overlapping peptides spanning all of the immunodominant proteins small T antigen, large T antigen, VP1, VP2, and VP3.

The peptide library used in the methods described herein are libraries of overlapping peptides that span all or a portion of a polyomavirus protein sequence. The peptide mixture may include three or more immunodominant epitopes. The peptides are at least 10 amino acids long (for example, 10-30 amino acids, 12-18 amino acids, 15-25 amino acids long). In some examples, the peptide mixture includes overlapping 15 amino acid peptides (15mers) that are arranged such that portions of the fragments and certain sequence of amino acids from the parent sequence occur in more than one peptide fragment of the mixture. The peptides overlap with one another by 10-15 amino acids (for example, overlap by 10, 11, 12, 13, 14, or 15 amino acids). In one specific example, the peptides in the peptide mixture overlap by 11 amino acids. The peptide library may comprise peptides of 8 to 20, such as 8, 9, 10, 11, 12, 13, 14, 15, 16, 17, 18, 19, or 20, contiguous amino acids of a full length antigen, although longer peptides may be used. With knowledge of a target antigen sequence, immunogenic peptide sequences predicted to bind to an MEW can be determined using publicly available programs. For example, an HLA binding motif program on the Internet (Bioinformatics and Molecular Analysis Section-BIMAS) can be used to predict epitopes of BKV immunodominant proteins, using routine methods.

In particular embodiments, the peptide mixture comprises pools of peptides of 15 amino acids in length with 11 amino acid overlap. A pool of peptides may comprise 50-200 peptides for each immunodominant protein, such as at least 50, 60, 70, 80, or 90 peptides per immunodominant protein. Exemplary peptide libraries for use in the present methods are commercially available as PEPMIX™ (JPT). For example, the PEPMIX™ BKV small T antigen comprise a pool of 41 peptides derived from a peptide scan through Small t antigen (Swiss-Prot ID: P03082), PEPMIX™ BKV large T antigen comprises a pool of 170 peptides derived from a peptide scan (15mers with 11 aa overlap) through Large T antigen (Swiss-Prot ID: P14999), PEPMIX™ BKV VP3 comprises a pool of 56 peptides derived from a peptide scan (15mers with 11 aa overlap) through Minor capsid protein VP2, isoform VP3 (Swiss-Prot ID: P03094), PEPMIX™ BKV VP2 comprises a pool of 85 peptides derived from a peptide scan (15mers with 11 aa overlap) through Minor capsid protein VP2 (Swiss-Prot ID: P03094), and PEPMIX™ BKV VP1 comprises a pool of 88 peptides derived from a peptide scan (15mers with 11 aa overlap) through Major capsid protein VP1 (Swiss-Prot ID: P14996).

In one embodiment 5 ng to 10 µg of peptide or each peptide library are employed per ml of culture, such as 5, 50, 100, 150, 200, 250, 300, 350, 400, 450, 500, 1500, 2000, 3000, 4000, 5000, 6000, 7000 or 8000 ng/ml, particularly 5000 ng of each peptide pool is used to stimulate cells (e.g., about $1 \times 10^6$ to about $75 \times 10^6$ cells, particularly 5 µg of each peptide pool per $50 \times 10^6$ cells).

The culture may comprise two or more cytokines such as IL-7, IL-15, and IL-2. In particular aspects, the culture comprises IL-7, IL-15, and IL-2. In some examples, the one or more cytokines are added to the culture medium at a concentration of about 2 ng/ml to about 100 ng/ml (for example, about 2 ng/ml to about 50 ng/ml, about 5 ng/ml to about 20 ng/ml, or about 10 ng/ml to about 20 ng/ml). In other examples, the one or more cytokines are added to the culture medium at a concentration of about 5-100 U/ml (such as about 10 U/ml to about 50 U/ml, about 20 U/ml to about 100 U/ml, or about 10 U/ml to about 20 U/ml). In particular aspects, IL-7 is present in the culture at a concentration of about 1 to 25 ng/mL, such as about 5, 10, or 15 ng/mL, particularly about 10 ng/mL. IL-2 may be present at a concentration of about 1 to 50 iU/mL, such as about 5, 10, 15, 20, 25, or 30 iU/mL, particularly about 20 iU/mL. Further, IL-15 may be present at a concentration of about 1 to 25 ng/mL, such as about 5, 10, or 15 ng/mL, particularly about 10 ng/mL. Additional cytokines may include, but are not limited to, IL-1, IL-4, IL-6, and IL-21.

The length of time for expansion of the BKV-specific T cells may be about 7-14 days, such as 8, 9, 10, 11, or 12 days. In particular aspects, the T cells are cultured in the presence of the peptide library and cytokines for about 10 days.

In one exemplary method, $50\times10^6$ PBMCs are suspended at $1\times10^6$ cells/mL in T cell expansion media (e.g., RPMI 1640 (45%), Clicks-EHAA media (45%), and human AB serum (10%), supplemented with GlutaMax at 2 mM). The cells are plated at a concentration of about $2\times10^6$ cells/mL per well in a 24-well plate for the first 4 days of expansion, followed by transfer to a tissue culture flask (e.g., 75 cm², 100 cm², or 150 cm² flask) for the remainder of the expansion of the BKV-specific T cells.

In particular embodiments, the method for expanding BKV-specific T cells does not comprise the use of a second population of cells which have been previously exposed to, stimulated with, or primed with BKV immunodominant proteins, such as the peptide library. For example, the second population of cells may comprise antigen presenting cells, dendritic cells, monocytes, PBMCs, or B cell lymphocytes that have been stimulated with the peptide library. Instead, embodiments of the present disclosure concern direct stimulation and expansion of BKV-specific T cells without the need for a pre-stimulation step.

The rapid expansion method may provide an increase in the number of BKV-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

T cell expansion may be evaluated by counting viable CD3$^+$ cells (i.e. the target population of cells is CD3$^+$). Viable cells can be tested by cell staining with Trypan blue (and light microscopy) or 7-amino-actinomycin D, vital dye emitting at 670 nm (or ViaProbe a commercial ready-to-use solution of 7AAD) and flow cytometry, employing a technique known to those skilled in the art. Where the stain penetrates into the cells, the cells are considered not viable. Cells which do not take up dye are considered viable.

Purity of the population of BKV-specific T cells can be determined using routine methods. In one example, purity is determined using markers present on the surface of BKV-specific T cells. Antigen-specific T cells are positive for the CD3 marker, along with the CD4 or CD8 marker, and IFN-γ (which is specific for activated T cells). For example, fluorescence activated cell sorting (FACS) can be used to identify (and sort if desired) populations of cells that are positive for CD3, CD4/CD8, and IFN-γ by using differently colored anti-CD3, anti-CD4, anti-CD8 and anti-IFN-γ. Briefly, stimulated BKV-specific T cells are incubated in the presence of anti-CD3, anti-CD4, anti-CD8 and anti-IFN-γ (each having a different fluorophore attached), for a time sufficient for the antibody to bind to the cells. After removing unbound antibody, cells are analyzed by FACS using routine methods.

The expanded BKV-specific T cells may be characterized to demonstrate specificity for BKV. The characterization may comprise determining the percentage of CD4$^+$ and/or CD8$^+$ T cells in the total population of CD3$^+$ T cells. The population may comprise at least 80% CD4$^+$ or CD8$^+$ T cells, such as at least 81, 82, 83, 84, 85, 86, 87, 88, 89, 90, 91, 92, 93, 93, 95, 96, 97, 98, 99, or 100% CD4$^+$ or CD8$^+$ T cells. In particular aspects, the population of BKV-specific T cells produced by the present methods comprises at least 10% IFNγ-producing cells, such as at least 11, 12, 13, 14, 15, 16, 17, 18, 19, 20, 21, 22, 23, 24, 25, or higher percentage of IFNγ-producing cells. In some aspects, the population of BKV-specific T cells produced by the present methods comprises at least 5% IL-2-producing cells, such as at least 6, 7, 8, 9, 10, 11, 12, 13, 14, 15, or higher percentage of IL-2-producing cells. Thus, the population of BKV-specific T cells produced by the present methods may comprise at least 2% cells positive for both IFNγ and IL2, particularly at least 3, 4, 5, 6, 7, 8, 9, 10, 11, 12, 13, 14, 15, or higher percentage of IFNγ$^+$IL2$^+$ T cells.

The cytotoxicity of the BKV-specific T cells may also be determined. Methods for determining cytotoxicity are known in the art, for example a $^{51}$Cr-release assay (for example see Walker et al., 1987; Qin et al., 2002; both herein incorporated by reference).

C. Genetically Engineered T Cells

The BKV-specific T cells may be genetically engineered to express antigen receptors such as engineered TCRs and/or chimeric antigen receptors (CARs). For example, the host cells (e.g, autologous or allogeneic T cells) are modified to express a T cell receptor (TCR) having antigenic specificity for a cancer antigen. Multiple CARs and/or TCRs, such as to different antigens, may be added to the BKV-specific T cells.

Suitable methods of modification are known in the art. See, for instance, Sambrook and Ausubel, supra. For example, the cells may be transduced to express a T cell receptor (TCR) having antigenic specificity for a cancer antigen using transduction techniques described in Heemskerk et al., 2008 and Johnson et al., 2009.

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autoreactive T cells will lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which will never lose the introduced TCR chains, causing a constantly present autoreactivity in the patient.

In some embodiments, the cells comprise one or more nucleic acids introduced via genetic engineering that encode one or more antigen receptors, and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

In some embodiments, the CAR contains an extracellular antigen-recognition domain that specifically binds to an antigen. In some embodiments, the antigen is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MEW) molecule.

Exemplary antigen receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO/2014055668 A1.

1. Chimeric Antigen Receptors

In some embodiments, the chimeric antigen receptor comprises: a) an intracellular signaling domain, b) a transmembrane domain, and c) an extracellular domain comprising an antigen binding region.

In some embodiments, the engineered antigen receptors include CARs, including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, incorporated herein by reference. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

In some embodiments, CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In certain embodiments of the chimeric antigen receptor, the antigen-specific portion of the receptor (which may be referred to as an extracellular domain comprising an antigen binding region) comprises a tumor associated antigen or a pathogen-specific antigen binding domain. Antigens include carbohydrate antigens recognized by pattern-recognition receptors, such as Dectin-1. A tumor associated antigen may be of any kind so long as it is expressed on the cell surface of tumor cells. Exemplary embodiments of tumor associated antigens include CD19, CD20, carcinoembryonic antigen, alphafetoprotein, CA-125, MUC-1, CD56, EGFR, c-Met, AKT, Her2, Her3, epithelial tumor antigen, melanoma-associated antigen, mutated p53, mutated ras, and so forth. In certain embodiments, the CAR may be co-expressed with a cytokine to improve persistence when there is a low amount of tumor-associated antigen. For example, CAR may be co-expressed with IL-15.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD 16, CD22, CD33, CD37, CD64, CD80, CD86, CD 134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

In certain embodiments, the platform technologies disclosed herein to genetically modify immune cells, such as NK cells, comprise (i) non-viral gene transfer using an electroporation device (e.g., a nucleofector), (ii) CARs that signal through endodomains (e.g., CD28/CD3-ζ CD137/CD3-ζ or other combinations), (iii) CARs with variable lengths of extracellular domains connecting the antigen-recognition domain to the cell surface, and, in some cases, (iv) artificial antigen presenting cells (aAPC) derived from K562 to be able to robustly and numerically expand CAR+ immune cells (Singh et al., 2008; Singh et al., 2011).

2. T Cell Receptor (TCR)

In some embodiments, the genetically engineered antigen receptors include recombinant TCRs and/or TCRs cloned from naturally occurring T cells. A "T cell receptor" or "TCR" refers to a molecule that contains a variable α and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form.

Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable α chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, (3-chain) can contain two immunoglobulin domains, a variable domain (e.g., $V_a$ or Vp; typically amino acids 1 to 116 based on Kabat numbering Kabat et al., "Sequences of Proteins of Immunological Interest, US Dept. Health and Human Services, Public Health Service National Institutes of Health, 1991, 5th ed.) at the N-terminus, and one constant domain (e.g., a-chain constant domain or $C_a$, typically amino acids 117 to 259 based on Kabat, β-chain constant domain or Cp, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR for a target antigen (e.g., a cancer antigen) is identified and introduced into the cells. In some embodiments, nucleic acid encoding the TCR can be obtained from a variety of sources, such as by polymerase chain reaction (PCR) amplification of publicly available TCR DNA sequences. In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, a high-affinity T cell clone can be isolated from a patient, and the TCR isolated. In some embodiments, the T-cells can be a cultured T-cell hybridoma or clone. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al., 2009 and Cohen et al., 2005). In some embodiments, phage display is used to isolate TCRs against a target antigen (see, e.g., Varela-Rohena et al., 2008 and Li, 2005). In some embodiments, the TCR or antigen-binding portion thereof can be synthetically generated from knowledge of the sequence of the TCR.

3. Suicide Genes

The CAR and/or TCR of the T cells of the present disclosure may comprise one or more suicide genes. The term "suicide gene" as used herein is defined as a gene which may be used to selectively target cells for killing. For example, as suicide gene may, upon administration of a prodrug, effect transition of a gene product to a compound which kills its host cell. Examples of suicide gene/prodrug combinations which may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The *E. coli* purine nucleoside phosphorylase, a so-called suicide gene which converts the prodrug 6-methylpurine deoxyriboside to toxic purine 6-methylpurine. Other examples of suicide genes used with prodrug therapy are the *E. coli* cytosine deaminase gene and the HSV thymidine kinase gene.

Exemplary suicide genes include CD20, CD52, EGFRv3, or inducible caspase 9. In one embodiment, a truncated version of EGFR variant III (EGFRv3) may be used as a suicide antigen which can be ablated by Cetuximab. Further suicide genes known in the art that may be used in the present disclosure include Purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-α, γ-lyase (MET), and Thymidine phosphorylase (TP).

4. Modification of Gene Expression

In some embodiments, the BKV-specific T cells of the present disclosure are modified to have altered expression of certain genes such as glucocorticoid receptor, TGFβ receptor (e.g., TGFβ-RII), and/or CISH. In one embodiment, the BKV-specific T cells may be modified to express a dominant negative TGFβ receptor II (TGFβRIIDN) which can function as a cytokine sink to deplete endogenous TGFβ.

In some embodiments, the altered gene expression is carried out by effecting a disruption in the gene, such as a knock-out, insertion, missense or frameshift mutation, such as biallelic frameshift mutation, deletion of all or part of the gene, e.g., one or more exon or portion therefore, and/or knock-in. For example, the altered gene expression can be effected by sequence-specific or targeted nucleases, including DNA-binding targeted nucleases such as zinc finger nucleases (ZFN) and transcription activator-like effector nucleases (TALENs), and RNA-guided nucleases such as a CRISPR-associated nuclease (Cas), specifically designed to be targeted to the sequence of the gene or a portion thereof.

Exemplary gRNA sequences for CRISPR-Cas mediated knockdown of NR3CS (glucocorticoid receptor) include Ex3 NR3C1 sG1 5-TGC TGT TGA GGA GCT GGA-3 (SEQ ID NO:1) and Ex3 NR3C1 sG2 5-AGC ACA CCA GGC AGA GTT-3 (SEQ ID NO:2). Exemplary gRNA sequences for TGF-beta receptor 2 include EX3 TGFBR2 sG1 5-CGG CTG AGG AGC GGA AGA-3 (SEQ ID NO:3) and EX3 TGFBR2 sG2 5-TGG-AGG-TGA-GCA-ATC-CCC-3 (SEQ ID NO:4). The T7 promoter, target sequence, and overlap sequence may have the sequence TTAATAC- GACTCACTATAGG (SEQ ID NO:5)+target sequence+gttt-tagagctagaaatagc (SEQ ID NO:6).

III. METHODS OF USE

The present disclosure further provides methods of treating polyomavirus-associated diseases with a therapeutically effective of the BKV-specific T cells provided herein. Accordingly, disclosed herein are methods of treating or inhibiting polyomavirus infection and/or polyomavirus-associated disease (such as PVAN, PML, hemorrhagic cystitis, TS, or MCC). The disclosed methods also include eliciting or enhancing an immune response against one or more polyomaviruses in the subject. In some embodiments the methods include administering to a subject (such as a subject having or at risk of polyomavirus infection or polyomavirus-associated disease) one or more of the disclosed polyomavirus antigen-specific T cells and/or modified DCs.

Polyomavirus infection is generally asymptomatic in healthy subjects. However, polyomavirus infection can occur or be reactivated in immunocompromised individuals and can cause significant morbidity, for example, due to polyomavirus-associated disease. Polyomavirus-associated nephropathy (PVAN; also called BK polyomavirus-associated nephropathy or BK virus nephritis) occurs in up to 10% of renal transplant recipients and is believed to be caused by BKV infection or reactivation of latent BKV infection. It causes kidney allograft dysfunction and may lead to loss of the allograft. Polyomavirus-associated hemorrhagic cystitis is characterized by inflammation of the bladder leading to dysuria, hematuria, and hemorrhage. It can occur in bone marrow transplant recipients and other individuals who are receiving immunosuppressants or other therapies which decrease immune system function. Trichodysplasia spinulosa (TS) is a skin condition characterized by development of papules, spines, and alopecia in the face. It occurs in immunocompromised patients and has recently been found to be associated with the presence of TS-associated polyomavirus (TSV). JCV can reactivate in immunocompromised individuals and can cause JCV-associated progressive multifocal leukoencephalopathy (PML), which is usually fatal. PML occurs in about 10% of patients suffering from HIV-induced AIDS and can also occur in other immunocompromised or immunosuppressed patients, including but not limited to patients treated with rituximab, natalizumab, alemtuzumab, or efalizumab. JCV can also cause urinary tract pathology in some organ transplant recipients. Another polyomavirus-associated diseases include Merkel cell carcinoma, hemorrhagic and nonhemorrhagic cystitis, ureteric stenosis, and nephritis (e.g., post-transplant).

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, lung cancer (including small-cell lung cancer, non-small cell lung cancer, adenocarcinoma of the lung, and squamous carcinoma of the lung), cancer of the peritoneum, gastric or stomach cancer (including gastrointestinal cancer and gastrointestinal stromal cancer), pancreatic cancer, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, and melanoma.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; lentigo malignant melanoma; acral lentiginous melanomas; nodular melanomas; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor;

meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's macroglobulinemia; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia; chronic lymphocytic leukemia (CLL); acute lymphoblastic leukemia (ALL); acute myeloid leukemia (AML); and chronic myeloblastic leukemia.

Particular embodiments concern methods of treatment of leukemia. Leukemia is a cancer of the blood or bone marrow and is characterized by an abnormal proliferation (production by multiplication) of blood cells, usually white blood cells (leukocytes). It is part of the broad group of diseases called hematological neoplasms. Leukemia is a broad term covering a spectrum of diseases. Leukemia is clinically and pathologically split into its acute and chronic forms.

In yet another embodiment, the subject is the recipient of a transplanted organ or stem cells and immune cells are used to prevent and/or treat rejection. In particular embodiments, the subject has or is at risk of developing graft versus host disease. GVHD is a possible complication of any transplant that uses or contains stem cells from either a related or an unrelated donor. There are two kinds of GVHD, acute and chronic. Acute GVHD appears within the first three months following transplantation. Signs of acute GVHD include a reddish skin rash on the hands and feet that may spread and become more severe, with peeling or blistering skin. Acute GVHD can also affect the stomach and intestines, in which case cramping, nausea, and diarrhea are present. Yellowing of the skin and eyes (jaundice) indicates that acute GVHD has affected the liver. Chronic GVHD is ranked based on its severity: stage/grade 1 is mild; stage/grade 4 is severe. Chronic GVHD develops three months or later following transplantation. The symptoms of chronic GVHD are similar to those of acute GVHD, but in addition, chronic GVHD may also affect the mucous glands in the eyes, salivary glands in the mouth, and glands that lubricate the stomach lining and intestines. Any of the BKV-specific T cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. T cells can be administered prior to transplantation, concurrently with transplantation, or following transplantation. In some embodiments, the T cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of T cells occurs 3-5 days prior to transplantation.

Methods are also disclosed for increasing the immune response, such as enhancing the immune system in a subject. Administration of the BKV-specific T cells disclosed herein will increase the ability of a subject to overcome pathological conditions, such as an infectious disease or a tumor, by targeting an immune response against BK virus. Therefore, by purifying and generating a purified population of selected BKV-specific T cells from a subject ex vivo and introducing a therapeutic amount of these cells into the same subject, or into another subject (allogeneic transplant), the immune system of the recipient subject will be enhanced by providing exogenous T cells that specifically recognize and direct an immune response against BK virus, thus treating the infection. In some examples, the donor and recipient are tissue-typed prior to administration of purified BKV-specific T cells into the recipient.

Subjects in need of enhanced immunity to polyomavirus include subjects who are immunocompromised, for example subjects who are infected with human immunodeficiency virus (HIV), subjects with SCID, diabetics, subjects who are receiving chemotherapy for cancer, subjects who are receiving immunosuppressive therapy (such as corticosteroids, a calcineurin inhibitor, such as tacrolimus, cyclosporine, or pimecrolimus, or other therapies that decrease immune system function, such as rituximab, natalizumab, efalizumab, or alemtuzumab), and/or elderly subjects (for example, human subjects 65 years of age or older). In some examples, subjects who are receiving immunosuppressive therapy include individuals who have received or are a candidate for an organ transplant (such as a renal transplant or other solid organ transplant or a bone marrow transplant). In a particular example, a subject in need of enhanced immunity to one or more polyomaviruses is a renal transplant recipient or a bone marrow (hematopoietic stem cell) transplant recipient. In other examples, subjects in need of enhanced immunity to polyomaviruses include those who are candidates for organ transplantation or those who are candidates for immunosuppressive therapy. In further examples, a subject in need of enhanced immunity to polyomaviruses may include a subject who has or is at risk for cancer (for example, prostate cancer, colon cancer, or bladder carcinoma).

In addition, methods of providing antiviral immunity to a subject are provided herein. Antiviral immunity can be provided to a subject by administration of BKV-specific T cells. Such administration to a recipient will enhance the recipient's immune response to the infection by providing T cells that are targeted to, recognize, and immunoreact with the viral antigen.

Infections in immune deficient people are a common problem in allograft stem cell recipients and in permanently immunosuppressed organ transplant recipients. The resulting T cell deficiency infections in these subjects are usually from reactivation of viruses already present in the recipient. For example, once acquired, most herpes group viruses (such as CMV, EBV, VZV, HSV) are dormant, and kept suppressed by T cells. However, when patients are immunosuppressed by conditioning regimens, dormant viruses can be reactivated. For example, CMV reactivation, Epstein Barr virus (EBV) reactivation which causes a tumor in B cells (EBV lymphoproliferative disease), and BK virus reactivation which causes hemorrhagic cystitis, can occur following immunosuppression. In addition, HIV infection and congenital immune deficiency are other examples of T cell immune deficiency. These viral infections and reactivations can complicate allo-stem cell transplants and organ transplants. In one example, BKV-specific T cells are administered to a subject who has had, or will receive, an allogeneic stem cell transplant or a solid organ transplant, such as kidney, liver, heart, or lung. For example, a therapeutic amount of BKV-specific T cells can be administered. In particular examples where the recipient receives an allogeneic stem cell transplant, the BKV-specific T cells are purified from the donor. In other examples where the recipient receives a solid organ transplant, BKV-specific T cells are purified from the recipient (autologous T cells). For example, a blood sample containing T cells can be obtained from the recipient prior to receiving the transplant.

Administration of a therapeutic amount of such cells can be used prophylactically to prevent reactivation of the virus in the recipient, or to treat an infection caused by reactivation of the virus. Such BKV-specific T cells can kill cells containing the infectious agent or assist other immune cells in fighting the infection.

In examples where T cells are transplanted from one individual into a recipient, the recipient's immune is depleted or ablated by any method known in the art. Examples of immunodepleting methods include, but are not limited to, the use of chemotherapy, radiotherapy and anti-lymphocyte antibodies such as Campath, ATG, ALG, OKT3. Such treatment is termed a conditioning regimen and is used to prepare the recipient to take (and not reject) the transplant of lymphocytes and marrow stem cells and to debulk the malignant disease if the recipient is being treated for a malignant disease. In one example, the recipient's immune system is depleted or ablated by the administration of total body irradiation and cyclophosphamide. In another example, fludarabine and other chemotherapy such as busulfan cyclophosphamide or melfalan is administered to deplete T cells and to debulk the malignant disease.

Purified BKV-specific T cells that specifically recognize a preselected target antigen are prepared by the methods disclosed herein. The cells can be tested for mycoplasma, sterility, endotoxin and quality controlled for function and purity prior to infusion into the recipient. If the BKV-specific T cells were cryopreserved, they are thawed prior to administration to the recipient.

A therapeutically effective amount of BKV-specific T cells are administered to the subject. Specific, non-limiting examples of a therapeutically effective amount of purified BKV-specific T cells include purified BKV-specific T cells administered at a dose of about $1 \times 10^5$ cells per kilogram of subject to about $1 \times 10^9$ cells per kilogram of subject, such as from about $1 \times 10^6$ cells per kilogram to about $1 \times 10^8$ cells per kilogram, such as from about $5 \times 10^6$ cells per kilogram to about $75 \times 10^6$ cells per kilogram, such as at about $25 \times 10^6$ cells per kilogram, or at about $50 \times 10^6$ cells per kilogram.

Purified BKV-specific T cells can be administered in single or multiple doses as determined by a clinician. For example, the cells can be administered at intervals of approximately 2 weeks depending on the response desired and the response obtained. In some examples, once the desired response is obtained, no further BKV-specific T cells are administered. However, if the recipient displays one or more symptoms associated with infection or the presence or growth of a tumor, a therapeutically effective amount of BKV-specific T cells can be administered at that time.

The BKV-specific T cells disclosed herein can be administered with a pharmaceutically acceptable carrier, such as saline. In some examples, other therapeutic agents are administered with the BKV-specific T cells. Other therapeutic agents can be administered before, during, or after administration of the BKV-specific T cells, depending on the desired effect. Exemplary therapeutic agents include, but are not limited to, anti-microbial agents, immune stimulants such as interferon-alpha, or peptide vaccines of the same antigen used to stimulate T cells in vitro. In a particular example, compositions containing BKV-specific T cells also include one or more therapeutic agents. After administration of the BKV-specific T cells, the response in the recipient can be monitored as determined appropriate by the clinician.

For example, viral infections can be monitored using methods known in the art. In one example, viral persistence is determined using a sample obtained from the recipient, such as blood or other body fluid. Antibody titers, cultures, and PCR are examples of techniques for following response to therapies. Using methods known in the art, whether viral nucleic acids are present in the subject can be determined, and whether virions are present in the subject can be determined using standard viral culture methods. In addition, the recipient can be monitored for a decrease or loss of symptoms and signs of viral infection, such as fever. In one example, administration of the BKV-specific T cells decreases the presence of virions or viral nucleic acids by at least 10%, for example at least 25%, at least 50%, at least 80%, at least 90%, at least 95% or even at least 99% as compared to an amount present before the administration of the cells.

In some examples, the BKV-specific T cells disclosed herein are administered to a subject at a dose of about $10^5$ CD3$^+$ cells/kg to about $10^9$ CD3$^+$ cells/kg, such as from about $10^6$ cells/kg to about $10^8$ cells/kg, such as from about $5 \times 10^6$ cells/kg to about $75 \times 10^6$ cells/kg, such as about $25 \times 10^6$ cells/kg, or about $50 \times 10^6$ cells/kg. In other examples, subject is administered about $10^5$ cells, about $10^6$ cells, about $10^7$ cells, about $10^8$ cells, about $10^9$ cells, about $10^{10}$ cells, about $10^{11}$ cells, or more. In particular non-limiting examples, the subject is administered at least about $10^5$ CD3$^+$ cells/kg, for example, about $10^6$-$10^7$ CD3$^+$ cells/kg. The BKV-specific T cells can be administered by any means known to one of skill in the art, either locally or systemically, such as by intravenous injection, intramuscular injection, subcutaneous injection, intraperitoneal injection, oral administration, nasal administration, or intradermal administration. In some specific embodiments, administration is by intravenous injection. In other specific embodiments, the BKV-specific T cells are administered by instillation into the peritoneal cavity, pleural cavity, or by injection into the cerebrospinal fluid (for example, by lumbar puncture).

BKV-specific T cells, such as those produced by the methods described herein, can be administered in a single dose or in multiple doses (such as 2, 3, 4, 5, or more doses), as determined by a clinician. In some examples, the cells are administered at intervals of approximately 1 day, 3 days, 1 week, 2 weeks, monthly, twice yearly, or yearly, depending on the response desired and the response obtained (such as induction of an immune response to one or more polyomaviruses and/or reduction or even elimination of one or more symptoms associated with one or more polyomavirus-related diseases). Either single or multiple doses will be administered, as determined by the research protocol and clinical status of the recipient.

In some examples, once the desired response is obtained (for example, establishment of a persisting repertoire of antigen-specific T cells or reduction of symptoms), no further BKV-specific T cells are administered. This response may be achieved with a single administration of BKV-specific T cells, in at least some examples. However, if there is evidence of non-persistence of the infused BKV-specific T cells and/or persisting symptoms associated with polyomavirus infection (including viremia and/or one or more symptoms of a polyomavirus-related disease) or if the subject has persisting immune deficiency, one or more additional administrations of a therapeutically effective amount of antigen-specific T cells can be administered. Immunization protocols (such as amount of T cells, number of doses and timing of administration) can be determined experimentally, for example by using animal models (such as mice or non-human primates), and/or by clinical testing in humans.

In some examples, other therapeutic agents are administered with the BKV-specific T cells (e.g., administered before, during, or after administration of the BKV-specific T cells), depending on the desired effect. Exemplary therapeutic agents include, but are not limited to, antiviral agents (for example, cidofovir, brincidofovir, or cytosine arabinoside (AraC)), antibiotics (for example, fluoroquinolines, such as ciprofloxacin or levofloxacin), immune stimulants (such as interferon-alpha), cytokines (such as IL-2), leflunomide, mefloquine, intravenous immunoglobulin (IVIG), or one or more peptides of the same antigen used to stimulate T cells in vitro. In a particular example, compositions containing the disclosed BKV-specific T cells also include one or more therapeutic agents.

A. Pharmaceutical Compositions

The present disclosure also provides therapeutic compositions that include the BKV-specific T cells. In particular examples, the BKV-specific T cells are placed in a therapeutic dose form for administration to a subject in need of them. In one example, such a therapeutic dose is administered to the subject in need of them, for example as disclosed herein.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutralactive hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The polyomavirus antigen-specific T cells disclosed herein can be administered with a pharmaceutically acceptable carrier, such as buffered saline. Standard procedures and buffers can be used. One of ordinary skill in the art can select one or more pharmaceutically acceptable carriers suitable for use with the cells disclosed herein. Remington: The Science and Practice of Pharmacy, The University of the Sciences in Philadelphia, Editor, Lippincott, Williams, & Wilkins, Philadelphia, Pa., $21^{st}$ Edition (2005), describes compositions and formulations suitable for pharmaceutical delivery of the cells herein disclosed. In general, the nature of the carrier will depend on the mode of administration being employed. For instance, parenteral formulations usually include injectable fluids that include pharmaceutically and physiologically acceptable fluids such as water, physiological saline, balanced salt solutions, aqueous dextrose, serum, plasma, serum substitutes, pharmacologically approved tissue culture medium supplemented with autologous serum or blood group AB serum from a blood bank, combinations thereof, or the like, as a vehicle. The carrier and composition can be sterile, and the formulation suited to the mode of administration.

In one example, the therapeutically effective amount includes a quantity of purified BKV-specific T cells sufficient to improve signs or symptoms a disease such as cancer, complications from a transplant (such as an infection), for example by increasing an immune response. In a particular example, it is an amount of purified BKV-specific T cells sufficient to increase an anti-tumor immune response, such as a graft-versus-leukemia (GVL) or graft-versus-tumor (GVT) response. In another particular example, it is an amount of donor cells depleted of donor T cells that recognize alloantigens of the recipient sufficient to decrease the effects or severity of GVHD, for example after allogeneic stem cell transplantation. A therapeutically effective amount of BKV-specific T cells can be administered in a single dose, or in several doses, for example every two weeks, during a course of treatment. However, the effective amount of purified BKV-specific T cells can depend on the subject being treated, the severity and type of the condition being treated, and the manner of administration. In one example, a therapeutically effective amount of purified BKV-specific T cells varies from about $10^5$ cells per kg body weight to about $10^9$ cells per kg body weight, for example at least $10^6$ cells per kg body weight.

The amount of cells effective in the treatment of a particular disorder or condition will depend on the nature of the disorder or condition, and can be determined by standard clinical techniques. In addition, in vitro assays can be employed to identify optimal dosage ranges. The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems.

Once the final formulation has been prepared it will be filled into a suitable container, for example an infusion bag or cryovial. In one embodiment, the process according to the present disclosure comprises the further step of filling the T cell population or pharmaceutical formulation thereof into a suitable container, such as an infusion bag and sealing the same. The container filled with the T cell population of the present disclosure or a pharmaceutical composition comprising the same may be frozen for storage and transport, for example is stored at about −135° C.

In one embodiment, the method of the present disclosure comprises the further step of freezing the T cell population of the present disclosure or a pharmaceutical composition comprising the same. In one embodiment, the "product" is frozen by reducing the temperature by 1° C. per minute to ensure the crystals formed do not disrupt the cell structure. This process may be continued until the sample has reached about −100° C. A product according to the present disclosure is intended to refer to a cultured cell population of the present disclosure or a pharmaceutical composition comprising the same. In one embodiment, the product is transferred, shipped, transported in a frozen form to the patient's location. The product may be provided in a form suitable for parenteral administration, for example, infusion, slow injection or bolus injection. In one embodiment, the formulation is provided in a form suitable for intravenous infusion.

B. Combination Therapies

In certain embodiments, the compositions and methods of the present embodiments involve BKV-specific T cells in combination with at least one additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

An immune cell therapy may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below the BKV-specific T cells are "A" and an anti-cancer therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate;

purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and angui dine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that additional immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p9'7), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies include are immune adjuvants, e.g., Mycobacterium bovis, Plasmodium falciparum, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; Pardoll, 2012; both incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. No. 8,735,553, U.S. Pat. No. 8,354,509, and U.S. Pat. No. 8,008,449, all incorporated herein by reference. Other PD-1 axis antagonists for use in the methods provided herein are known in the art such as described in U.S. Patent Application No. US20140294898, US2014022021, and US20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; Camacho et al., 2004; and Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof (see, e.g., WO 01/14424). In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. No. 5,844,905, U.S. Pat. No. 5,885,796 and International Patent Application Nos. WO1995001994 and WO1998042752; all incorporated herein by reference, and immunoadhesins such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

IV. ARTICLES OF MANUFACTURE OR KITS

An article of manufacture or a kit is provided comprising BKV-specific T cells is also provided herein. The article of manufacture or kit can further comprise a package insert comprising instructions for using the T cells to treat or delay progression of a polyomavirus-associated disease in an individual or to enhance immune function of an individual having cancer. Any of the BKV-specific T cells described herein may be included in the article of manufacture or kits. Suitable containers include, for example, bottles, vials, bags and syringes. The container may be formed from a variety of materials such as glass, plastic (such as polyvinyl chloride or polyolefin), or metal alloy (such as stainless steel or hastelloy). In some embodiments, the container holds the formulation and the label on, or associated with, the container may indicate directions for use. The article of manufacture or kit may further include other materials desirable from a commercial and user standpoint, including other buffers, diluents, filters, needles, syringes, and package inserts with instructions for use. In some embodiments, the article of manufacture further includes one or more of another agent (e.g., a chemotherapeutic agent, and anti-neoplastic agent). Suitable containers for the one or more agent include, for example, bottles, vials, bags and syringes.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Rapid Expansion of BKV-Specific T Cells

Figure 2:
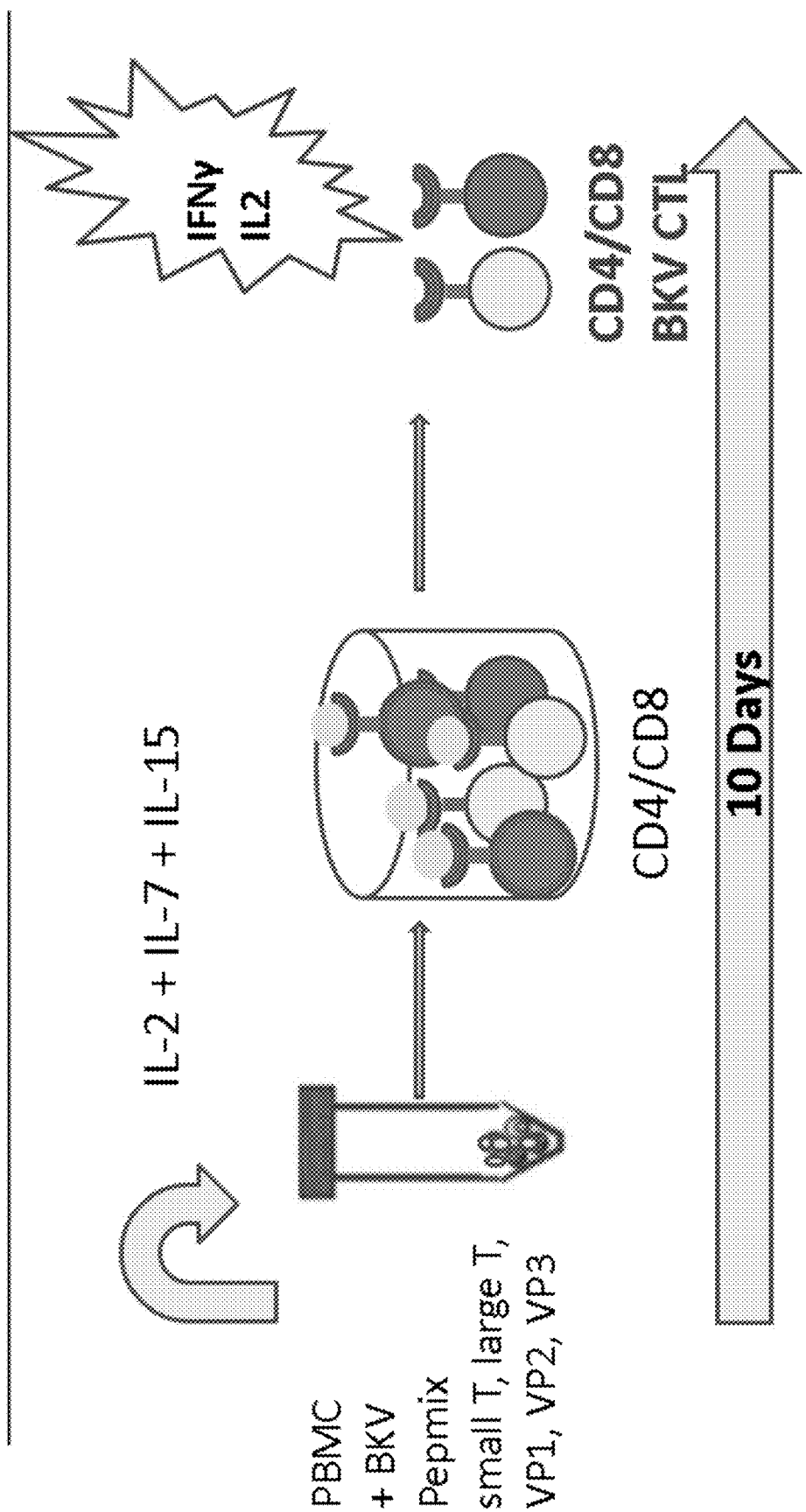
FIG. 2: Schematic depicting BKV-specific T cells rapid generation and expansion method. BKV-specific T cells are generated ex vivo by stimulating donor PBMCs with a peptide mixture comprising overlapping peptides from the 5 immunodominant proteins (small T antigen, large T antigen, VP1, VP2, and VP3).
Figure 3A:
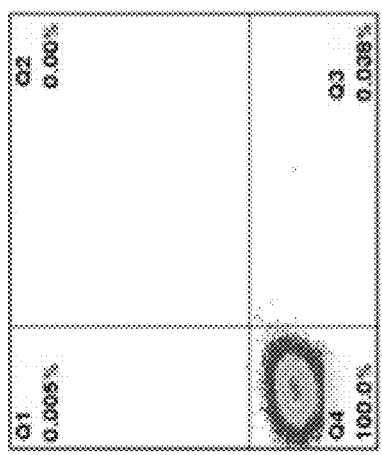
FIGS. 3A-3C.

Analysis was performed on adoptive immunotherapy using HLA-matched BKV-specific CTL BKV-CTLs generated by ex vivo expansion as depicted in FIG. 1. Pre-expansion frequency of BKV-specific CD4 and CD8 T cells producing IL-2 (0.038%) and producing IFNγ (0.005%) was found to be very low (FIG. 3A). A bank of BKV-specific CTLs were generated from 27 virus-immune healthy donors (mean age, 55; range, 25 to 75 years). Mononuclear cells enriched from donor buffy coats were stimulated with BKV peptide mix from capsid proteins VP1, VP2, VP3, large T antigen (LT) and small T antigen (ST) in the presence of IL-2, IL-7 and IL-15 for 14 days (FIG. 2A). At the end of culture, the cells were harvested and cryopreserved until use.

Figure 3B:
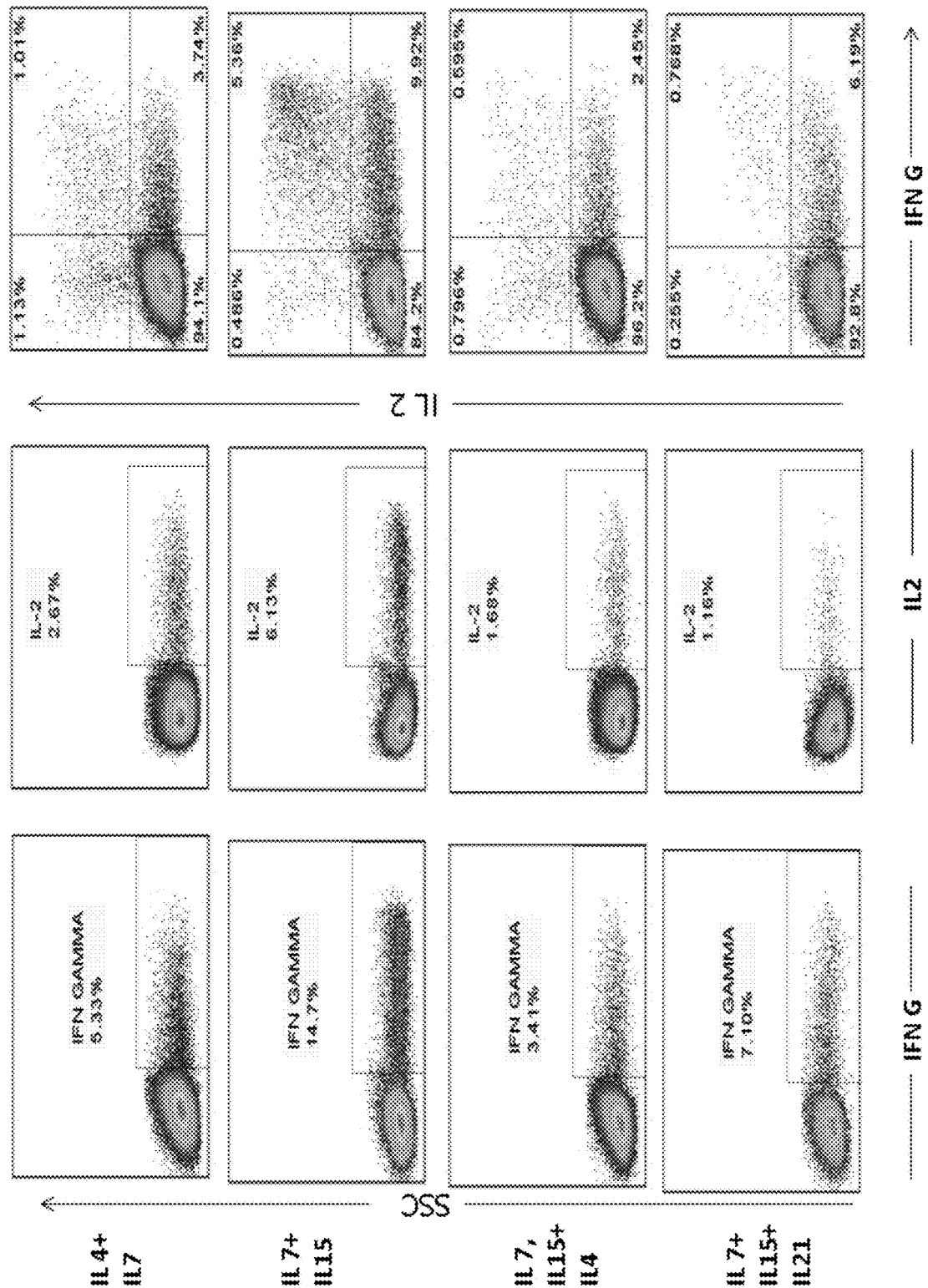

Post-expansion frequency of BKV-specific T cells expanded with the 5 peptide mix and various cytokines combinations was determined (FIG. 3B). It was found that the combination of IL4+IL7 produced only 5.33% T cells positive for IFNγ, 2.67% cells positive for IL2, and 1.01% percent cells positive for both IFNγ and IL2. The other combinations of cytokines did not produce much higher percentages of BKV-specific T cells. On the other hand, the combination of IL7 and IL15 surprisingly resulted in almost 15% IFNγ-positive cells and 5.36% cells positive for both IFNγ and IL2.

Figure 3C:
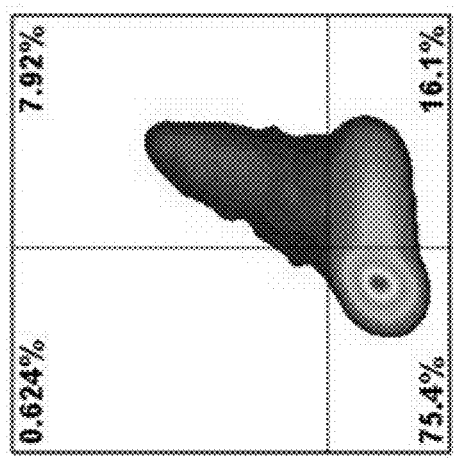
Figure 3C:
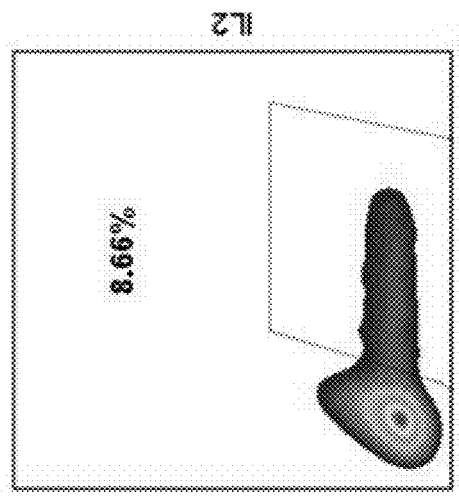
Figure 3C:
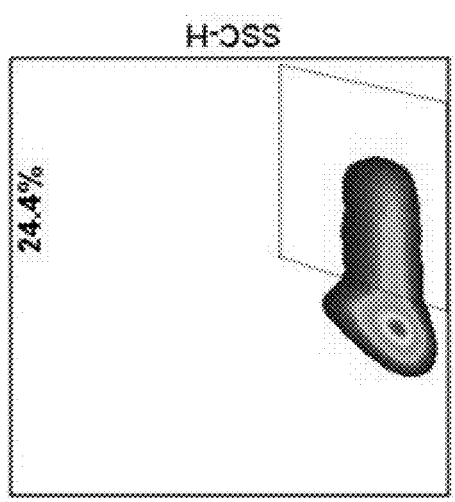

Interestingly, the post-expansion frequency of BKV-specific T cells expanded with the 5 peptide mix and IL2+IL7+IL15 (FIG. 3C) for 10 days resulted in even higher frequencies of BKV-specific CD4 and CD8 T cells as measured by their ability to produce IFNγ and IL2 in response to BKV. Specifically, the rapid expansion method produced almost 25% (24.4%) cells produced IFNγ and almost 9% (8.66%) cells produced IL-2. Almost 8% (7.92%) of the expanded cells produced both IFNγ and IL2.

TABLE 1

Characterization of BKV-specific T cells from 27 donors (5-25 doses per line). The infused dose is less than $1 \times 10^5$ T-cells/kg.

| Variable [%] | Median | Range |
| --- | --- | --- |
| $CD3^+CD4^+$ T cells | 42.9 | 17.7-76.6 |
| $CD3^+CD8^+$ T cells | 47.1 | 14.7-84.0 |
| $CD4^+IFNγ^+$ T cells | 14.4 | 3.0-41.9 |
| $CD4^+IL2^+$ T cells | 10.4 | 1.9-29.7 |
| $CD4^+IL2^+IFNγ^+$ T cells | 8.7 | 1.9-29.9 |
| $CD8^+IFNγ^+$ T cells | 2.2 | 0.6-60.6 |
| $CD8^+IL2^+$ T cells | 1.5 | 0.3-20.1 |
| $CD8^+IL2^+IFNγ^+$ T cells | 1.4 | 0.5-9.2 |
| TNC infused $\times 10^5$/Kg | 1.29 | 0.4-9.2 |

Figure 6:
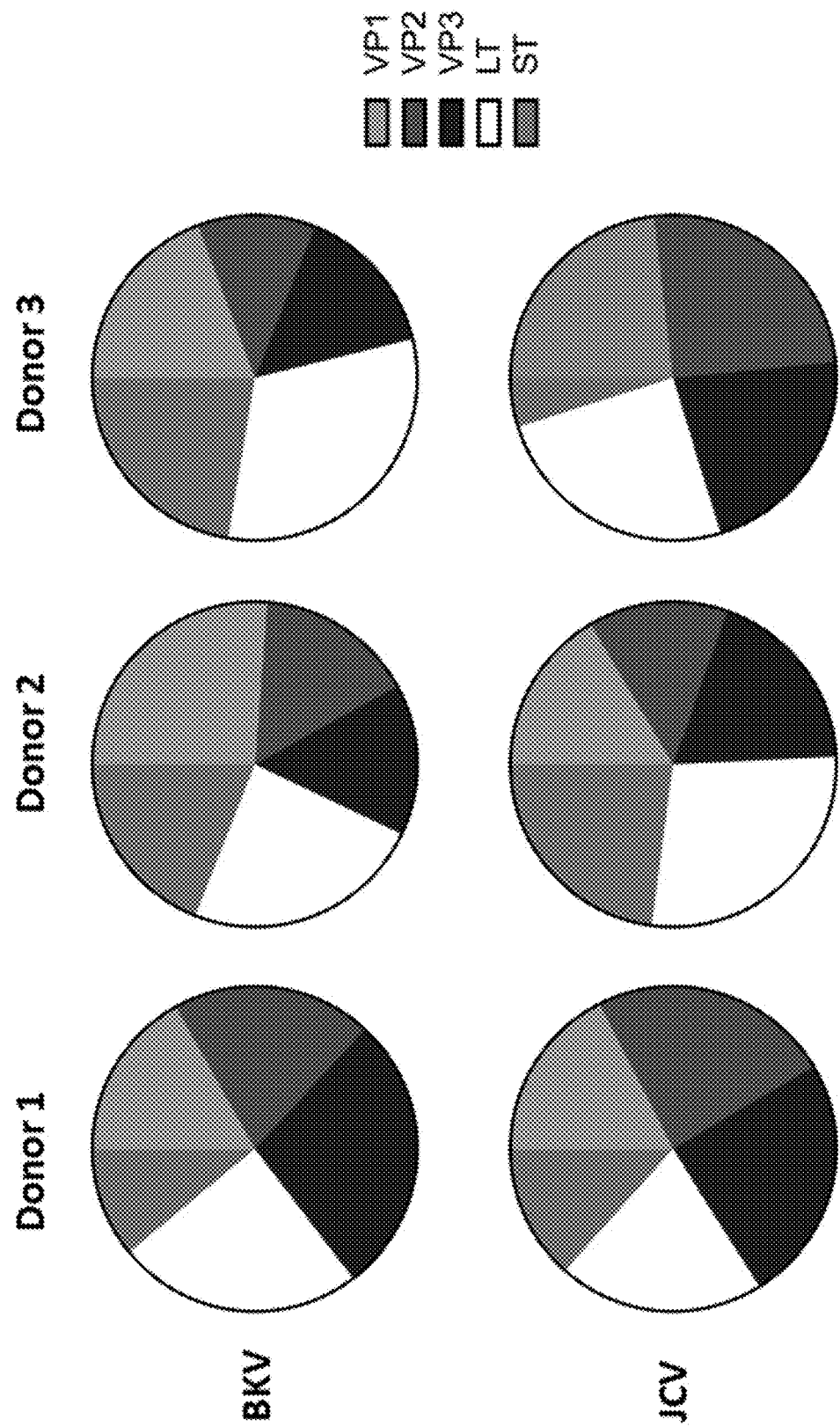
FIG. 6. BKV CTLs also recognize JCV VP1, VP2, VP3, ST and LT, as shown in three different donors

There were approximately equal numbers of CD4 and CD8 cells in the ex vivo expanded donor product. The method was able to achieve high frequencies of interferon gamma and interleukin 2 secreting CD4 T cells as the BK T cell response was CD4 dominant. Ex vivo expanded BKV CTLs also recognize JCV VP1, VP2, VP3, LT and ST (FIG. 6).

TABLE 2

| Characteristics at time of infusion, N = 19. | |
| --- | --- |
| Baseline Grade hemorrhagic cystitis | 3 (3-4) |
| Viral Load (copies/ml) | Urine 9.8 × 10$^7$ (1.3 × 10$^7$-1 × 10$^{10}$) Blood 491 (0-468,000) |
| Cidofovir | 1/19 |
| Nephrostomy | 1/19 |
| CBI | 3/19 |

Patients with symptomatic BKV cystitis after HSCT for leukemia or lymphoma were eligible for the study. Patients with acute GVHD grades II-IV, those receiving >0.5 mg/kg systemic steroids/day or on treatment with cidofivir or leflunomide were excluded. A search for the most closely HLA-matched donor was initiated through the MDACC cell therapy donor bank. A donor was used if at least 1/6 HLA matched at the HLA-A, —B, and DRB1 level. The baseline grade of hemorrhagic cystitis was 2, with viral loads shown here. 1 patient was being treated with cidofivir, 1 patient had nephrostomies and 3 patients were undergoing continuous bladder irrigation at the time of treatment. BKV-specific T cells were infused directly after thawing. Patients could receive up to 2 infusions.

BKV PCR and clinical symptoms were monitored every 2 weeks for 28 days after infusion. Response to treatment was defined as:
  Complete response (CR): Complete resolution of symptoms and gross hematuria.
  Partial response (PR): Decrease in grade of HC from 3 (urinary blood clots) or 4 (red cell transfusion requirement/renal impairment) to 2 (macroscopic hematuria) or 3 respectively.
  Stable disease (SD): Changes insufficient to qualify as PR or progression.
  Progression: Increase in symptoms or worsening hematuria.

10 patients (2 HLA-matched related, 5 HLA-matched unrelated and 3 haploidentical HSCT recipients) received BKV-CTLs for BK cystitis. The median number of BKV-specific CD3$^+$IFNγ$^+$ and CD3$^+$IL-2$^+$ T cells infused was 10e3/kg and 4.8e3/kg. The ratio of BKV-specific CD4$^+$/CD8+ T cells in the infused product was 7.8 (range 3.1-22.1). There were no infusion-related adverse effects. Based on end-organ response, BKV-CTLs controlled infection in 9/9 evaluable patients with BKV cystitis (4 CRs and 5 PRs). One patient was not evaluable due to disease relapse, sepsis and anuria. All patients achieved a response by day 14 post-infusion. Two of 5 patients with PR received a second BK CTL infusion from a different donor. One had an initial PR to the first CTL infusion but symptoms progressed after 6 weeks. A second infusion resulted in a PR with reduction in BKV PCR and symptoms. The other patient achieved CR within 28 days of the second infusion. The time to second infusion was 6 and 3 weeks, respectively. The response in all patients was sustained.

No infusion related toxicity and no graft failure were observed. There was 1 death due to relapsed AML, which was present prior to CTL administration. 1 patient developed stage 2 overall grade 3 lower GI GVH, 1 patient developed stage 2, grade 2 upper GI GVH both were successfully treated with systemic steroids. One patient developed stage 1 grade 1 skin GVH successfully treated with topical steroids.

Since BKV and JCV share significant genomic and protein similarities, one cord blood transplant recipient with JC encephalitis was treated with partially HLA-matched BK CTLs, with significant improvement in viral load, symptoms and imaging abnormalities on MM.

Following infusion, high frequencies of polyfunctional BKV-specific CD4+ and CD8+ T-cells, capable of producing IL-2, IFN-gamma and TNF-alpha were detected. These cells were shown to successfully traffic to the CNS in the PML patient. The response was mainly CD4+ T cell dominant, reflecting the composition of the infused BKV T cell line.

De novo grade 2-4 acute graft versus host disease (aGVHD) occurred in 1/10 patients. The patient developed grade 2 duodenal GVHD 14 days following infusion. A second patient had recurrence of a prior skin GVHD and developed grade 2 aGVHD 9 days after infusion. Both were successfully treated with 1 mg/kg/day systemic steroids.

This analysis demonstrates the safety, feasibility and efficacy of administration of most closely HLA-matched BKV CTLs for the treatment of BKV cystitis in HSCT patients. The response rate of 100% in the first 11 patients treated with BKV CTLs is promising.

TABLE 3

| Comparison of characteristics for responders vs. non-responders. | | |
| --- | --- | --- |
| | CR/PR (n = 14) | SD/Progression (n = 4) |
| Baseline Grade HC | 3 (3-4) | 3 (3-4) |
| HLA Match (out of 10 alleles) | 4 of 10 alleles | 5 of 10 alleles |
| Systemic Steroid | 2/14 | 2/4 |
| Topical/Budesonide | 5/14 | 2/4 |
| Days post SCT | 144 (34-742) | 72.5 (27-121) |
| ALC day of Infusion | 0.56 (0.24-1.46) | 0.175 (0.2-0.42) |
| Frequencies of CD4 | 42.9 (26-76.6) | 34.45 (19.3-60.8) |
| Frequencies of CD8 | 45.6 (20.32-74) | 59.8 (37.9-84) |
| IL2$^+$ CD4 | 15.5 (1.9-52) | 7.62 (5.4-28.7) |
| IFNγ$^+$ CD4 | 12.65 (3-41.9) | 11.47 (8.8-41.9) |
| IL2+ CD8 | 1.1 (0.8-9.7) | 0.95 (0.8-4.7) |
| IFNγ$^+$ CD8 | 2.05 (0.6-13.6) | 2.05 (0.6-4.3) |
| TNC (×10$^6$) | 10 (6-121) | 11 (8-12) |

Figure 4:
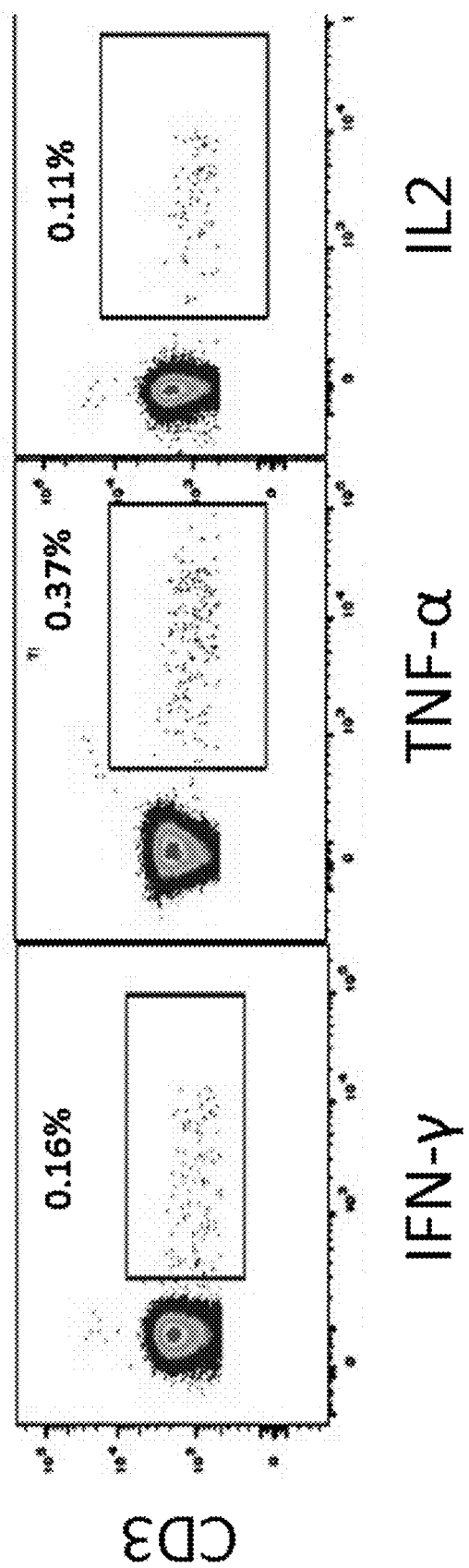
FIG. 4: Frequencies of poly-functional BKV-specific T cells in the peripheral blood of patients 2 weeks after infusion.

Immune correlative studies were performed to assess the persistence of BKV-specific CTLs. As shown in FIG. 4, significant frequencies of poly-functional BKV CTLs were present in the peripheral blood of patients 2 weeks after infusion. Further, persistence of the BKV-specific T cells was seen for at least 1 month post-infusion.

Figure 5A:
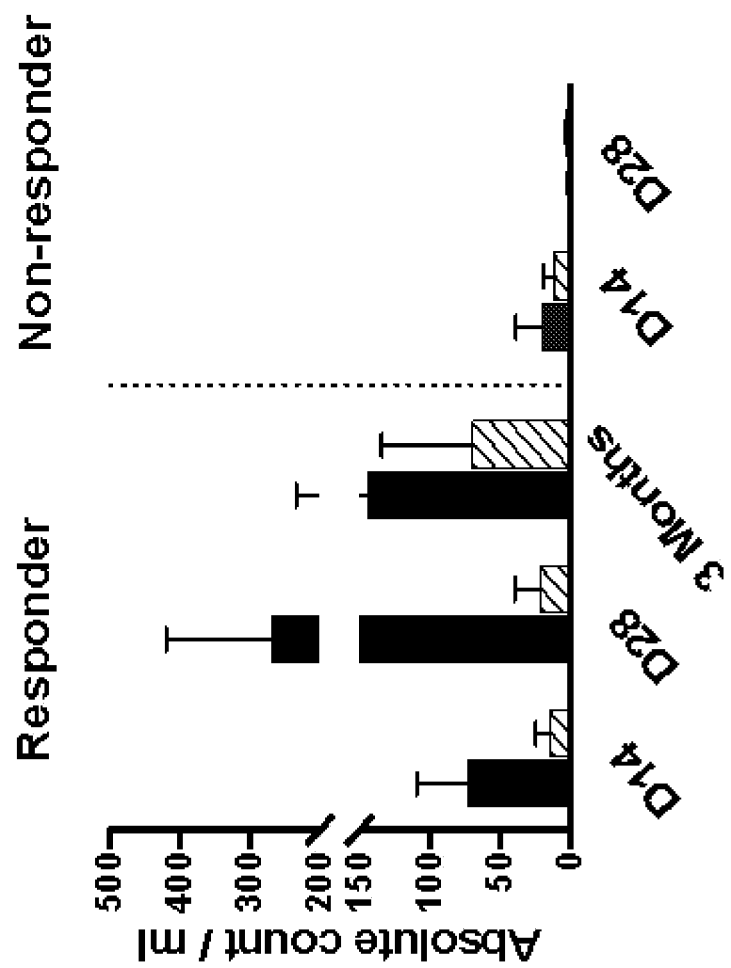
FIGS. 5A-5B.
Figure 5B:
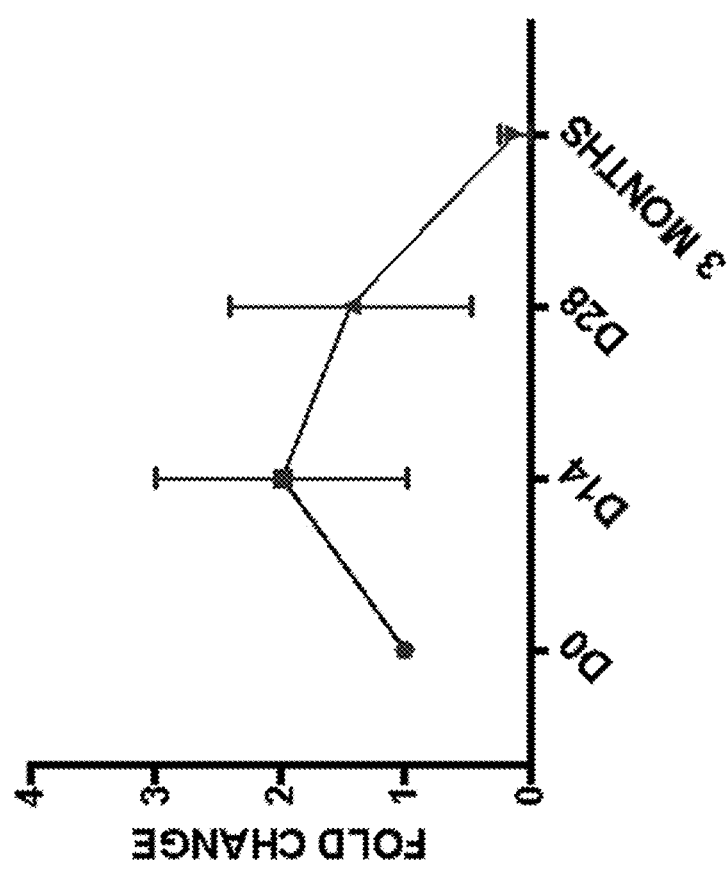

Analysis of the BKV CTL expansion was performed in samples obtained from patients who were responders or non-responders. It was observed that the response in patients was associated with BKV CTL expansion (FIG. 5A)>

TABLE 4

| Responses to date of 27 patients treated and evaluated. | |
| --- | --- |
| Responses (27) | |
| Complete Response | 20 |
| Partial Response | 1 |
| ORR | 84% (CI 0.65-0.94) |
| Time to response | 11 days |

Example 2—Use of Expanded Allogeneic BKV-Specific T Cells to Target Progressive Multifocal Leukoencephalopathy Progressive multifocal leukoencephalopathy (PML) is a rare and often fatal demyelinating disorder of central nervous system caused by JC virus reactivation in patients with severe defects of cellular immunity. JC virus is genetically similar to BK virus. Both JC and BK virus express large tumor antigen (LT), small tumor antigen (ST), and the capsid proteins, VP1, VP2 and VP3 during replication. Due to antigenic epitope homology, ex vivo expanded BK virus specific T cells can also target JCV, especially for VP1 and LT. We developed a rapid, effective and GMP-compliant BK virus specific cytotoxic T lymphocyte (CTL) expansion method from peripheral blood mononuclear cells. Donor mononuclear cells were stimulated with a BK virus peptide mix in the presence of IL-2, IL-7 and IL-15 for 14 days. At the end of culture, the cells were harvested and cryopreserved until use. BKV CTLs also recognize JCV VP1. VP2, VP3, ST and LT. The first two cases of PML treated with BK virus specific CTL from the most closely HLA-matched donor are described.

Case 1.

A 32-year-old female with a diagnosis of FLT3+ acute myeloid leukemia underwent double cord blood transplantation. Her post-transplant course was complicated by acute graft versus host disease involving skin and gastrointestinal tract, HHV-6 infection and BK virus related hemorrhagic cystitis. Twenty months after transplantation she presented with left-sided extremity weakness, slurred speech and mental confusion. The physical examination revealed ataxic gait and weakness of left lower extremity. Mill revealed abnormal pattern of parenchymal enhancement and signal abnormality in the posterior fossa, predominantly involving cerebellum and brain stem. Lumbar puncture revealed low levels of JC virus DNA (130 copies/ml). Repeat MM three weeks later showed progression in the peduncle and right cerebellum with an increase in the CSF JC virus load to 700 copies/ml. At this point the patient received $10_5$/kg BKV-specific CTLs expanded from a 3/6 HLA-matched allogeneic donor. There was no infusion-related toxicity. Two weeks later, there was a significant reduction in the JC virus titer to 78 copies/ml (limit of detection 72 copies/mL). HLA $BW6_+$ donor $CD4_+$ and CD8+ T-cells could be detected in the CSF 2 weeks after infusion, confirming that BK virus CTLs can home to inflammatory sites in the central nervous system. The lymphocytes in CSF showed a distinct phenotypic profile, mainly composed of recipient $CD56_{bright}$ NK cells and a mixture of donor and recipient CD4+ and CD8+ T cells. Donor T cells in CSF expressed very high levels of PD1 and CXCR3 compared to peripheral blood T-cells. Four weeks from the infusion, the neurological symptoms have resolved and repeat MM confirmed near complete resolution of the lesions. The patient received a second CTL infusion 3 weeks after the first for persistent low positive JCV in the CSF. The patient remains essentially asymptomatic 20 months after BK virus specific CTL infusion with undetectable JC virus DNA titers in the CSF. Donor T cells continue to be present in the CSF.

Case 2.

A 73-year-old female with JAK2 positive myeloproliferative disorder on treatment with ruxolitinib for 8 years presented with altered mental state, blurred vision and unsteady gait. MRI revealed parieto-occipital subcortical signals in left hemisphere extending to the posterior temporal lobe suggestive of PML. JC virus load in the CSF was 230,000 copies/ml. She received a 2/6 HLA-matched allogeneic BK virus specific CTLs. Three weeks after infusion JC virus titer in the CSF decreased to 5,200 copies/ml and her condition stabilized. The MRI remained stable. Donor-derived CD4+ and CD8+ T cells were detected in the CSF, with high expression of PD1 and inflammatory chemokines on T cells. The patient received a second dose of BK virus specific CTL from the same donor one month after the first infusion. The CSF viral load reduced further to 800 copies/ml but the there was no clinical or radiological improvement, suggestive of irreversible CNS damage. In this proof-of-principle study, ex vivo expanded BK virus specific CTLs were used to target PML, a disease without viable treatment strategies and with a universally fatal outcome. Both patients showed a remarkable reduction in the viral load and there was near complete resolution of symptoms and MM findings in one case. Use of third party partially HLA-matched BK virus specific CTLs to treat PML holds promise.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allander et al, *J. Virol.* 81:4130-4136, 2007.
Austin-Ward and Villaseca, *Revista Medica de Chile,* 126 (7):838-845, 1998.
Ausubel et al., *Current Protocols in Molecular Biology,* Greene Publishing Associates and John Wiley & Sons, N Y, 1994.
Bukowski et al., *Clinical Cancer Res.,* 4(10):2337-2347, 1998.
Camacho et al. *J Clin Oncology* 22(145): Abstract No. 2505 (antibody CP-675206), 2004.
Chothia et al., *EMBO J.* 7:3745, 1988.
Christodoulides et al., *Microbiology,* 144(Pt 11):3027-3037, 1998.
Cohen et al. *J Immunol.* 175:5799-5808, 2005.
Davidson et al., *J. Immunother* 21(5):389-398, 1998.
Davila et al. *PLoS ONE* 8(4): e61338, 2013.
European patent application number EP2537416
Fedorov et al., *Sci. Transl. Medicine,* 5(215), 2013.
Gaynor et al, *PLoS Pathog.* 3:e64, 2007.
Gerdmann et al., *Molecular Therapy,* 20(8): 1622-32, 2012.
Hanibuchi et al., *Int. J. Cancer,* 78(4):480-485, 1998.
Heemskerk et al. *Hum Gene Ther.* 19:496-510, 2008.
Hellstrand et al., *Acta Oncologica,* 37(4):347-353, 1998.
Hollander, *Front. Immun.,* 3:3, 2012.
Hui and Hashimoto, *Infection Immun.,* 66(11):5329-5336, 1998.
Hurwitz et al. *Proc Natl Acad Sci USA* 95(17): 10067-10071, 1998.
International Patent Publication No. WO1995001994
International Patent Publication No. WO1998042752
International Patent Publication No. WO2000037504

International Patent Publication No. WO200014257
International Patent Publication No. WO2001014424
International Patent Publication No. WO2006/121168
International Patent Publication No. WO2009/101611
International Patent Publication No. WO2009/114335
International Patent Publication No. WO2010/027827
International Patent Publication No. WO2011/066342
International Patent Publication No. WO2012/129514
International Patent Publication No. WO2013/071154
International Patent Publication No. WO2013/123061
International Patent Publication No. WO2013/166321
International Patent Publication No. WO2013126726
International Patent Publication No. WO2014/055668
International Patent Publication No. WO2014031687
International Patent Publication No. WO2015016718
Janeway et al, Immunobiology: The Immune System in Health and Disease, 3$^{rd}$ Ed., Current Biology Publications, p. 433, 1997.
Johnson et al. *Blood* 114:535-46, 2009.
Jores et al., *PNAS U.S.A.* 87:9138, 1990.
Leal, M., *Ann N Y Acad Sci* 1321, 41-54, 2014.
Lefranc et al., *Dev. Comp. Immunol.* 27:55, 2003.
Mokyr et al. *Cancer Res* 58:5301-5304, 1998.
Pardoll, *Nat Rev Cancer*, 12(4): 252-64, 2012.
Parkhurst et al. *Clin Cancer Res.* 15: 169-180, 2009.
Qin et al. *Acta Pharmacol. Sin.* 23(6):534-8, 2002.
Qin et al., *Proc. Natl. Acad. Sci. USA*, 95(24):14411-14416, 1998.
Sadelain et al., *Cancer Discov.* 3(4): 388-398, 2013.
Sambrook et al., *Molecular Cloning: A Laboratory Manual*, 3$^{rd}$ ed., Cold Spring Harbor Press, Cold Spring Harbor, N.Y. 2001.
Singh et al., *Cancer Research*, 68:2961-2971, 2008.
Singh et al., *Cancer Research*, 71:3516-3527, 2011.
Tosato, Current Protocols in Immunology, Ed Coligan et al, Wiley, 1994.
Turtle et al., *Curr. Opin. Immunol.*, 24(5): 633-39, 2012.
U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,844,905
U.S. Pat. No. 5,885,796
U.S. Pat. No. 6,207,156
U.S. Pat. No. 6,410,319
U.S. Pat. No. 7,109,304
U.S. Pat. No. 7,446,190
U.S. Pat. No. 8,008,449
U.S. Pat. No. 8,017,114
U.S. Pat. No. 8,119,129
U.S. Pat. No. 8,329,867
U.S. Pat. No. 8,354,509
U.S. Pat. No. 8,735,553
U.S. Patent Publication No. 2002131960
U.S. Patent Publication No. 2005/0260186
U.S. Patent Publication No. 2006/0104968
U.S. Patent Publication No. 20110008369
U.S. Patent Publication No. 20130149337
U.S. Patent Publication No. 2013287748
U.S. Patent Publication No. 2014022021
U.S. Patent Publication No. 20140294898
van der Meijden et al, *PLoS Pathog.* 6:E1001024, 2010.
Varela-Rohena et al. *Nat Med.* 14: 1390-1395, 2008.
Walker et al. *Nature* 328:345-8, 1987.
Wong et al., *Cytotherapy*, 4: 65-76, 2002.
Wu et al., *Cancer*, 18(2): 160-75, 2012.

What is claimed is:

1. An ex vivo method for rapid expansion of BK virus (BKV)-specific T cells comprising the step of:
directly stimulating in culture a population of isolated peripheral blood mononuclear cells (PBMCs) in the presence of a mixture of peptides, IL-7, IL-15, and IL-2, wherein the mixture of peptides comprises overlapping peptides spanning at least 3 immunodominant BKV proteins selected from the group consisting of small T antigen, large T antigen, VP1, VP2, and VP3, thereby producing a cultured cell population comprising expanded BKV-specific T cells wherein the culture does not comprise isolated antigen presenting cells (APCs) pre-stimulated with the mixture of peptides, and wherein the peptides, IL-7, IL-15, and IL-2 are added to the culture substantially simultaneously.

2. The method of claim 1, wherein the BKV-specific T cells comprise CD8+ T cells and CD4+ T cells.

3. The method of claim 1, wherein the method comprises a culturing step for 8-14 days.

4. The method of claim 1, wherein the APCs are dendritic cells, monocytes, or B lymphocytes.

5. The method of claim 1, wherein the overlapping peptides have a length of 10-20 amino acids.

6. The method of claim 1, wherein the PBMCs are cultured in the presence of overlapping peptides spanning 4 of the immunodominant proteins.

7. The method of claim 1, wherein the PBMCs are cultured in the presence of overlapping peptides spanning small T antigen, large T antigen, VP1, VP2, and VP3.

8. The method of claim 1, wherein the IL-2 is present at a concentration of 10 IU/mL to 200 IU/mL, the IL-7 is present at a concentration of 1 ng/ml to 25 ng/ml and the IL-15 is present at 1 ng/ml to 25 ng/ml.

9. The method of claim 2, wherein at least 15% of the total CD4+ T cells in the cultured cell population secrete IFNγ in response to BKV.

10. The method of claim 9, wherein at least 20% of the total CD4+ T cells in the cultured cell population secrete IFNγ in response to BKV.

11. The method of claim 2, wherein at least 5% or 8% of the total CD4+ T cells in the cultured cell population secrete IL-2 in response to BKV.

12. The method of claim 2, wherein at least 5% or 7% of the total CD4+T cells in the cultured cell population secrete IL-2 and IFNγ in response to BKV.

13. The method of claim 1, wherein the peptide mixture and cytokines are not changed after initiation of the culturing step.

14. A method for treating a polyomavirus-associated disease in a subject comprising administering an effective amount of BKV-specific T cells produced by the method of claim 1 to the subject.

15. The method of claim 14, wherein the polyomavirus-associated disease is progressive multifocal leukoencephalopathy (PML), Merkel cell carcinoma (MCC), polyomavirus-associated nephropathy (PVAN), hemorrhagic cystitis, JC encephalitis, or trichodysplasia spinulosa (TS).

16. The methods according to claim 8, wherein the IL-2 is present at a concentration of about 20 IU/ml or about 50 IU/ml, the IL-7 is present at a concentration of about 10 ng/ml, and the IL-15 is present at a concentration of about 10 ng.ml.

17. The method according to claim 1, wherein the culturing occurs without the addition of exogenous IL-1, IL-4, IL-6 and/or IL-21.

18. The method according to claim 1, wherein the culturing occurs without the addition of exogenous cytokines other than IL-2, IL-7 and IL-15.

19. The method of claim 14, wherein the subject is administered a single dose of an unfractionated cultured ell population produced according to claim 1 comprising at least about $1\times10^5$ CD3+ T cells per kilogram of body weight.

20. The method of claim 14, wherein the subject is administered multiple dosed of unfractionated cultured cell population produced according to claim 1 comprising at least $1\times10^5$ CD3+ T cells kilogram of body weight multiple times.

21. The method according to claim 20, wherein the subject is administered a dose of an unfractionated cultured cell population produced according to claim 1 comprising at least about $1\times10^5$ CD3+ T cells per kilogram of body weight once weekly, once dvery other week or once per month.

* * * * *

UNITED STATES PATENT AND TRADEMARK OFFICE
CERTIFICATE OF CORRECTION

PATENT NO. : 10,821,134 B2
APPLICATION NO. : 15/982942
DATED : November 3, 2020
INVENTOR(S) : Katy Rezvani Page 1 of 1

It is certified that error appears in the above-identified patent and that said Letters Patent is hereby corrected as shown below:

In the Claims

At Column 45, Claim number 19, Line number 5, delete "ell" and replace with cell.

At Column 45, Claim number 21, Line number 17, delete "dvery" and replace with every.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*